United States Patent
Deklotz et al.

(10) Patent No.: US 12,109,199 B2
(45) Date of Patent: Oct. 8, 2024

(54) TOPICAL mTOR INHIBITORS FOR CUTANEOUS PROLIFERATIVE AND VASCULAR CONDITIONS

(71) Applicant: Georgetown University, Washington, DC (US)

(72) Inventors: Cynthia Marie Carver Deklotz, Bethesda, MD (US); Robert A. Silverman, Arlington, VA (US)

(73) Assignee: Georgetown University, Washington, DC (US)

( * ) Notice: Subject to any disclaimer, the term of this patent is extended or adjusted under 35 U.S.C. 154(b) by 1099 days.

(21) Appl. No.: 16/967,457

(22) PCT Filed: Feb. 6, 2019

(86) PCT No.: PCT/US2019/016758
§ 371 (c)(1),
(2) Date: Aug. 5, 2020

(87) PCT Pub. No.: WO2019/156999
PCT Pub. Date: Aug. 15, 2019

(65) Prior Publication Data
US 2021/0177810 A1 Jun. 17, 2021

Related U.S. Application Data

(60) Provisional application No. 62/626,779, filed on Feb. 6, 2018.

(51) Int. Cl.
*A61K 31/436* (2006.01)
*A61K 9/00* (2006.01)

(52) U.S. Cl.
CPC .......... *A61K 31/436* (2013.01); *A61K 9/0014* (2013.01)

(58) Field of Classification Search
CPC ..... A61K 31/436; A61K 9/0014; A61P 17/02; A61P 35/00; A61P 9/14
See application file for complete search history.

(56) References Cited

U.S. PATENT DOCUMENTS

| | | | |
|---|---|---|---|
| 9,555,034 B2 | 1/2017 | Seykora | |
| 2013/0225631 A1 | 8/2013 | Teng et al. | |

FOREIGN PATENT DOCUMENTS

| | | |
|---|---|---|
| WO | WO 2008/022256 A2 | 2/2008 |
| WO | WO 2014/177123 A1 | 11/2014 |
| WO | WO 2018/031789 A1 | 8/2016 |

OTHER PUBLICATIONS

Haemel (Arch Dermatol, 146, 7, Jul. 2010) (Year: 2010).*
Ravikumar et al. (MJAFI, 1998, 54, 73-75). (Year: 1998).*
Gianfreda et al. (Blood, 2015, 126(10):1163-1171) (Year: 2015).*
Cooper et al. (Pediatr Blood Cancer, 2016, 63, 358-360) (Year: 2016).*
Peters (STL vol. 19, 4, Aug. 1, 2014) (Year: 2014).*
Cappel (The Pediatric Upper Extremity, 2014, p. 1-38). (Year: 2014).*
ClinicalTrials.gov, "A Randomized Trial to Study Combined Pulsed Dye Laser and Rapamycin Treatment of Port Wine Stain Birthmarks", ClinicalTrials.gov Identifier: NCT00830466, obtained from url: https://www.clinicaltrials.gov/ct2/show/NCT00830466.
Deklotz et al., "Dramatic improvement of facial angiofibromas in tuberous sclerosis with topical rapamycin: optimizing a treatment protocol", Arch Dermatol., Sep. 2011, 147(9): 1116-1117.
International Preliminary Report on Patentability for PCT International Application No. PCT/US2019/016758, dated Aug. 11, 2020, 8 pages.
International Search Report and Written Opinion for PCT International Application No. PCT/US2019/016758, dated Apr. 11, 2019, 10 pages.
Zaytseva et al., "mTOR inhibitors in cancer therapy", Cancer Letters, Jun. 1, 2012, 319(1): 1-7.

* cited by examiner

*Primary Examiner* — Umamaheswari Ramachandran
(74) *Attorney, Agent, or Firm* — Lathrop GPM LLP; Judith Stone-Hulslander; Tanya D'Souza

(57) ABSTRACT

Methods for the treatment of cutaneous vascular conditions and cutaneous proliferative conditions are provided. The methods employ topical administration of mammalian target of rapamycin (mTOR) inhibitors such as sirolimus (rapamycin) and everolimus. Conditions treatable by the disclosed methods include venolymphatic malformations, acne, acne rosacea, periorificial dermatitis, acne vulgaris, cutaneous capillary malformation-arteriovenous malformation (CM-AVM) syndrome, RASopathies, Langerhans cell histiocytosis, non-Langerhans cell histiocytosis, scars, hypertrophic or keloidal scars, Proteus syndrome, PIK3CA-related overgrowth spectrum (PROS), PTEN hamartoma tumor syndromes, cutaneous malignancies and tumors associated with PI3K/AKT/mTOR mutations, keratodermas, acanthosis nigricans, Birt-Hogg-Dube syndrome, Brooke-Speigler syndrome, cylindromas, and epidermal nevi. Also provided are formulations and pharmaceutical compositions having mTOR inhibitor as principal therapeutically active ingredient useful in practicing the methods.

9 Claims, No Drawings

TOPICAL mTOR INHIBITORS FOR CUTANEOUS PROLIFERATIVE AND VASCULAR CONDITIONS

RELATED APPLICATIONS

This application is a 35 U.S.C. § 371 filing of International Patent Application No. PCT/US2019/016758, filed Feb. 6, 2019, which claims benefit of priority to U.S. Provisional Patent Application No. 62/626,779, filed Feb. 6, 2018, the entire contents of which are incorporated herein by reference.

BACKGROUND

Sirolimus (rapamycin) inhibits the mammalian target of rapamycin (mTOR), which is a serine/threonine protein kinase whose activity has been reported to lead to cell proliferation, cytokine production, and angiogenesis. Orally administered rapamycin is approved for systemic use in a variety of clinical applications. However, there is no standard or commercially available topical formulation.

SUMMARY

Provided are methods and compositions useful for treating any of a variety of cutaneous proliferative conditions and cutaneous vascular conditions by topical administration of an mTOR inhibitor.

An aspect of the invention is a method of treating a cutaneous proliferative condition, comprising topically administering to an affected area of a subject in need thereof a therapeutically effective amount of a mammalian target of rapamycin (mTOR) inhibitor, thereby treating the condition.

In certain embodiments, the cutaneous proliferative condition excludes any one or more of trichoepithelioma and familial multiple discoid fibroma.

In certain embodiments, the cutaneous proliferative condition is selected from the group consisting of histiocytosis, Langerhans cell histiocytosis, histiocytosis X, eosinophilic granuloma, Letterer-Siwe disease, Hand-Schuller-Christian syndrome, Hashimoto-Pritzker syndrome, non-Langerhans cell histiocytosis (non-LCH), benign cephalic histiocytosis (BCH), juvenile xanthogranuloma, xanthoma disseminatum, necrobiotic xanthogranuloma, generalized eruptive histiocytoma, progressive nodular histiocytoma, indeterminate cell histiocytosis, multicentric reticulohistiocytosis, sinus histiocytosis with massive lymphadenopathy, scars, hypertrophic scars, keloids, Proteus syndrome, PTEN hamartoma tumor syndromes, Cowden syndrome, Babbayan-Riley-Ruvalcaba syndrome, cutaneous malignancies and tumors associated with PI3K/AKT/mTOR mutations, keratoderma, acanthosis nigricans, Birt-Hogg-Dubé syndrome, Brooke-Spiegler syndrome, cylindromas, and epidermal nevi.

In certain embodiments, the cutaneous proliferative condition is Langerhans cell histiocytosis (LCH).

In certain embodiments, the cutaneous proliferative condition is non-Langerhans cell histiocytosis (non-LCH).

In certain embodiments, the cutaneous proliferative condition is benign cephalic histiocytosis (BCH).

In certain embodiments, the affected area comprises at least a portion of any one or more of the head, face, and neck.

In certain embodiments, the mTOR inhibitor is selected from the group consisting of sirolimus, everolimus, and a combination thereof. In certain embodiments, the mTOR inhibitor is sirolimus. In certain embodiments, the mTOR inhibitor is everolimus.

In certain embodiments, the mTOR inhibitor inhibits only mTORC1 activity. In certain embodiments, the mTOR inhibitor inhibits only mTORC2 activity. In certain embodiments, the mTOR inhibitor inhibits both mTORC1 and mTORC2 activity.

In certain embodiments, the mTOR inhibitor is provided as a topical formulation comprising 0.01% to 10% (w/w) of the mTOR inhibitor in a pharmaceutically acceptable carrier.

In certain embodiments, the mTOR inhibitor is provided as a topical formulation comprising 0.05% to 5% (w/w) of the mTOR inhibitor in a pharmaceutically acceptable carrier.

In certain embodiments, the mTOR inhibitor is provided as a topical formulation comprising 0.1% to 2% (w/w) of the mTOR inhibitor in a pharmaceutically acceptable carrier.

In certain embodiments, the mTOR inhibitor is provided in combination with a PI3K inhibitor.

In certain embodiments, the mTOR inhibitor is provided as a combination mTOR/PI3K dual inhibitor.

In certain embodiments, the subject is a human less than 18 years of age.

In certain embodiments, the subject is a human at least 18 years of age.

An aspect of the invention is a method of treating a cutaneous vascular condition, comprising topically administering to an affected area of a subject in need thereof a therapeutically effective amount of a mammalian target of rapamycin (mTOR) inhibitor, thereby treating the condition.

In certain embodiments, the cutaneous vascular condition excludes any one or more of facial angiofibromas in tuberous sclerosis, microcystic lymphatic malformations, and port wine stains.

In certain embodiments, the cutaneous vascular condition is selected from the group consisting of PIK3CA-related overgrowth spectrum (PROS), venolymphatic malformations, acne, acne rosacea, periorificial dermatitis, fibrous papules, acne vulgaris, cutaneous capillary malformation-arteriovenous malformation (CM-AVM) syndrome, and RASopathies, including neurofibromas.

In certain embodiments, the cutaneous vascular condition is PIK3CA-related overgrowth spectrum (PROS).

In certain embodiments, the cutaneous vascular condition is venolymphatic malformations.

In certain embodiments, cutaneous conditions that have a vascular or proliferative aspect to them include acne rosacea, periorificial dermatitis, acne vulgaris, scars, hypertropic scars, and keloidal scars.

In certain embodiments, the affected area comprises at least a portion of any one or more of the head, face, and neck.

In certain embodiments, the mTOR inhibitor is selected from the group consisting of sirolimus, everolimus, and a combination thereof. In certain embodiments, the mTOR inhibitor is sirolimus. In certain embodiments, the mTOR inhibitor is everolimus.

In certain embodiments, the mTOR inhibitor inhibits only mTORC1 activity. In certain embodiments, the mTOR inhibitor inhibits only mTORC2 activity. In certain embodiments, the mTOR inhibitor inhibits both mTORC1 and mTORC2 activity.

In certain embodiments, the mTOR inhibitor is provided as a topical formulation comprising 0.01% to 10% (w/w) of the mTOR inhibitor in a pharmaceutically acceptable carrier.

In certain embodiments, the mTOR inhibitor is provided as a topical formulation comprising 0.05% to 5% (w/w) of the mTOR inhibitor in a pharmaceutically acceptable carrier.

In certain embodiments, the mTOR inhibitor is provided as a topical formulation comprising 0.1% to 2% (w/w) of the mTOR inhibitor in a pharmaceutically acceptable carrier.

In certain embodiments, the mTOR inhibitor is provided in combination with a PI3K inhibitor.

In certain embodiments, the mTOR inhibitor is provided as a combination mTOR/PI3K dual inhibitor.

In certain embodiments, the subject is a human less than 18 years of age.

In certain embodiments, the subject is a human at least 18 years of age.

DETAILED DESCRIPTION mTOR

The mammalian target of rapamycin (mTOR), also known as the mechanistic target of rapamycin and FK506-binding protein 12-rapamycin-associated protein 1 (FRAP1), belongs to the family of phosphatidylinositol-3-kinase (PI3K)-related kinases (PIKKs). Members in this family are large in size (>2,500 amino acids) and harbor a kinase domain at their C-terminals that shares sequence similarity to phosphatidylinositol-3-kinase (PI3K). Despite having the sequence signature of a lipid kinase, mTOR is a protein kinase that phosphorylates threonine and serine residues in its substrates. In cells mTOR serves as the catalytic subunits of two multi-protein complexes termed as the mTOR complex 1 (mTORC1) and complex 2 (mTORC2). TORC1 is a major downstream component of the PI3K/AKT pathway that relays the signals from tumor suppressors PTEN, LKB1 and TSC1/2, and oncoproteins PI3K and AKT. Downstream, mTORC1 controls cellular biogenesis through regulation of protein synthesis and turnover. It phosphorylates eIF4E binding protein 1 (4EBP1) and ribosomal protein S6 kinase (S6K), two factors involved in translation initiation. Its activity controls protein turnover through repressing autophagy. mTORC2 is also involved in the PI3K/AKT pathway but its function is independent of mTORC1. It phosphorylates and stimulates AKT activation, and hence plays a critical role in AKT mediated cell survival.

mTOR Inhibitors

As used herein, an "mTOR inhibitor" refers to an agent that can reduce the expression and/or activity of mTOR, including association of mTOR with its substrates. A number of mTOR inhibitors, including sirolimus and everolimus, are known and in clinical use. Sirolimus (also known as rapamycin) is the prototype of the first generation of mTOR inhibitors. It is a macrocyclic lactone that contains two binding moieties that are essential for its action. One moiety binds to FKBP12, a small cytosolic protein that displays peptidylprolyl isomerase activity. At pharmacologically relevant concentration, rapamycin imposes no significant effect on the function of FKBP12, but binding with FKBP12 allows it to interact with its mechanistic target, mTOR, to form a ternary complex. The rapamycin-FKBP12 dimer binds to mTOR in a region (FKBP12-rapamycin binding domain) that is outside of the kinase domain. As such, the binding itself does not inhibit the kinase activity of mTOR. It is believed that the binding interferes with the association of the kinase with its substrates, although the precise mechanism remains to be elucidated. Despite the presence of mTOR in both mTORC1 and mTORC2, rapamycin only inhibits mTORC1 activity.

Following entry into the cytoplasm, sirolimus and everolimus bind to FK binding protein (FKBP) and are believed to modulate the activity of mTOR. The mTOR inhibits interleukin-2 (IL-2)-mediated signal transduction, resulting in cell-cycle arrest in the G1-S phase. Sirolimus and everolimus block the response of T- and B-cell activation by cytokines, which prevents cell-cycle progression and proliferation. In contrast, tacrolimus and cyclosporine work by other mechanisms to inhibit the production of cytokines.

Sirolimus was first developed into an immunosuppressive drug for its potent action in blocking T-cell activation. It was approved by the FDA in 1997 for use in transplantation to prevent allograft rejection, and in 2003 for use in coronary-artery stents to prevent restenosis.

Although the anti-cancer activity of rapamycin was documented in early 1980s, its application in cancer therapy was not exploited until late 1990s, when several analogs of the drug, which often are referred to as rapalogs, were developed. Rapamycin is poorly water soluble, which affects its bioavailability.

Everolimus is the 40-O-(2-hydroxyethyl) derivative of sirolimus and works similarly to sirolimus as an inhibitor of mTOR. It is currently used as an immunosuppressant to prevent rejection of organ transplants and in the treatment of renal cell cancer and other tumors. Much research has also been conducted on everolimus as targeted therapy for use in a number of cancers. It is marketed by Novartis under the trade names Zortress (USA and Europe and other countries) in transplantation medicine and Afinitor and Votubia in oncology.

Temsirolimus is a derivative and prodrug of sirolimus. It is formulated as an intravenous drug approved for use in the treatment of renal cell carcinoma.

Ridaforolimus (AP23573, MK-8669), also known as deforolimus, is an investigational mTOR inhibitor being co-developed by Merck Sharp & Dohme (MSD) and Ariad Pharmaceuticals.

mTOR inhibitors can include so-called second generation mTOR inhibitors. Second generation mTOR inhibitors are known as ATP-competitive mTOR kinase inhibitors. Zaytseva Y. et al., *Cancer Letters* 319(1): 1-7 (2012). mTORC1/mTORC2 dual inhibitors are designed to compete with ATP in the catalytic site of mTOR. They inhibit all of the kinase-dependent functions of mTORC1 and mTORC2 and therefore, block the feedback activation of PI3K/AKT signaling, unlike rapalogs that only target mTORC1. These types of inhibitors have been developed and several of them are being tested in clinical trials. Like rapalogs, they decrease protein translation, attenuate cell cycle progression, and inhibit angiogenesis in many cancer cell lines and also in human cancer. In fact they have been proven to be more potent than rapalogs.

Cutaneous Proliferative Conditions

As used herein, a "cutaneous proliferative condition" refers to refers to a skin condition characterized by abnormal or undesirable proliferation of principally non-vascular structures or non-vascular tissue in skin. As used herein, "skin" refers to any or all of epidermis, dermis, and hypodermis, and appendages, glands, and blood and lymphatic vessels therein. See, for example, Bloom and Fawcett, A Textbook of Histology, 10$^{th}$ Ed., W. B. Saunders, Philadelphia, 1975. The skin condition characterized by abnormal or undesirable proliferation of principally non-vascular structures or non-vascular tissue in skin can be a cutaneous manifestation of a multisystemic or more general condition that is not confined to skin.

For purposes of this disclosure, to the extent that any cutaneous vascular condition as defined herein is considered to be, or can be considered to be, a cutaneous proliferative condition, such cutaneous vascular condition is to be understood also to be included among cutaneous proliferative conditions in accordance with the invention.

Cutaneous proliferative conditions include, without limitation, various forms of histiocytosis, hypertrophic and keloidal scars, Proteus syndrome, PTEN hamartoma tumor syndromes, Cowden syndrome, Babbayan-Riley-Ruvalcaba syndrome, cutaneous malignancies and tumors associated with PI3K/AKT/mTOR mutations, keratodermas, acanthosis nigricans, Birt-Hogg-Dubé syndrome and its related tumors, Brooke-Spiegler syndrome, cylindromas, and epidermal nevi.

In certain embodiments, the cutaneous proliferative condition excludes any one or more of trichoepithelioma and familial multiple discoid fibroma.

Somatic activating mutations in the PI3K/AKT/mTOR pathway have been implicated in numerous conditions, including Proteus syndrome (caused by a somatic gain of function mutation in AKT1) and PIK3CA-Related Overgrowth Spectrum (PROS). As these are due to overactivation of the PI3K/AKT/mTOR pathway, treatment with an mTOR inhibitor to decrease that overactivation would be expected to be effective. Due to this direct pathway involvement and favorable results of studies disclosed in the Examples herein, the inventor expects that the cutaneous features in these syndromes will respond to treatment with topical mTOR inhibitor such as topical rapamycin.

Negative regulators of the PI3K/AKT/mTOR signaling pathway include PTEN and TSC1/TSC2 (found in Tuberous Sclerosis Complex). Loss-of function mutations in PTEN are known to cause PTEN hamartoma tumor syndromes, including Cowden syndrome and Bannayan-Riley-Ruvalcaba syndrome, both of which have specific cutaneous findings. Due to this direct pathway involvement and favorable results of studies disclosed in the Examples herein, the inventor expects that the cutaneous features in these PTEN syndromes will respond to treatment with topical mTOR inhibitor such as topical rapamycin.

Somatic mutations in this pathway are also linked with several tumors and malignancies. If such tumors and malignancies are limited to the skin and soft tissue, the inventor expects that topical mTOR inhibitor such as topical rapamycin will be effective in the treatment of those tumors and cutaneous malignancies.

As used herein, "histiocytosis" refers to disorders that are characterized by infiltrates containing either Langerhans cell histiocytes (the X-type histiocytoses) or non-Langerhans cell histiocytes (the non-X or non-LCH histiocytoses).

There are two large families of histiocytoses based on various classification schema—X-type histiocytosis or Langerhans cell histiocytosis (LCH), and non-LCH histiocytoses, the latter of which may be subdivided into the juvenile xanthogranuloma (JXG) family (which have the phenotype of dermal dendritic cells, being positive for factor XIIIa, fascia, MS-1, and CD68); and multicentric reticulohistiocytosis and sinus histiocytosis with massive lymphadenopathy (SHML; Rosai-Dorfman disease) along with other histiocytoses, which are felt not to be in the JXG family of non-LCH histiocytoses. A diagnosis is most often established by typical clinical features, a compatible histology, and an evolution typical for that disorder.

Langerhans Cell Histiocytosis (LCH)—As used herein, "Langerhans cell histiocytosis" (LCH) refers to a clonal proliferative disease of Langerhans cells that express an immunophenotype positive for 5100, CD1a and Langerin (CD207), and which contain cytoplasmic Birbeck granules. Because Langerin is the major protein of Birbeck granules, Langerin immunostaining can be used as a substitute for demonstration of Birbeck granules by electron microscopy. LCH represents a disease spectrum with four prominent but overlapping syndromes: Letterer-Siwe disease; Hand-Schüller-Christian disease; eosinophilic granuloma; and congenital self-healing reticulohistiocytosis (also known as Hashimoto-Pritzker disease or Hashimoto-Pritzker syndrome). Disease expression ranges from mild, sometimes asymptomatic, single-organ involvement to severe, progressive multisystem disease.

Letterer-Siwe disease, Hand-Schüller-Christian disease, and eosinophilic granuloma were described in the early twentieth century. In 1953, Lichtenstein grouped these three disorders into a single entity called "histiocytosis X." In 1973, Hashimoto and Pritzker described the entity congenital self-healing reticulohistiocytosis Immunologic and ultrastructural studies confirmed the relationship of the pathologic cells in histiocytosis X and congenital self-healing reticulohistiocytosis to Langerhans cells, providing basis for their combined classification as "Langerhans cell histiocytoses".

LCH occurs worldwide and most commonly develops in children ages 1-3 years, though disease can develop at any age. The reported incidence of LCH varies widely. However, an annual incidence of at least five per million children is often quoted, with the adult incidence suspected to be less than one-third that of children. LCH is more common in boys, with a male:female ratio of nearly 2:1. In adults, there may be a slight female predominance. At least a small subset of LCH appears to be hereditary.

Until recently, the pathogenesis of LCH was unknown. Viral and immunologic etiologies had long been considered, although to date no studies have demonstrated a primary immune abnormality in patients with LCH and there has been no consistent detection of viral genomes in LCH tissue. In 2010, a significant percentage (57%) of LCH specimens were shown to harbor the BRAF V600E mutation, as has been described in cutaneous melanomas. This finding strongly suggested that LCH is neoplastic and raised the possibility of the therapeutic use of BRAF inhibitors in the future. In addition, several studies have demonstrated clonal $CD1a^+$ histiocytes in all LCH tissue tested. Based upon these results, as well as the presence of oncogenic BRAF mutations, LCH is now widely regarded as a clonal neoplastic disorder.

Several studies have demonstrated elevated levels of cytokines in lesions of patients with LCH, including TNF-α, interferon-γ, granulocyte-monocyte colony-stimulating factor (GM-CSF) and interleukin (IL)-1, IL-2, IL-4 and IL-10; these cytokines and interleukins are thought to promote various disease-related symptoms and morbidity, rather than being responsible for the development of disease.

For mild single-system skin disease (if treatment is required), topical corticosteroids, topical antimicrobials, narrowband UVB, PUVA (psoralen and long-wave ultraviolet (UVA) radiation), and topical nitrogen mustard (mechlorethamine) have been reported to be effective in case series, although potential side effects must be considered. For more extensive disease, thalidomide may be effective.

Localized bone lesions can be treated effectively with curettage. Symptomatic recurrent or new lesions, or those with a significant risk of fracture, cosmetic defect or functional abnormality, may require treatment with radiation. Treatment options for less problematic bone tumors include oral nonsteroidal anti-inflammatory drugs (NSAIDs) and intralesional corticosteroid injections.

Multisystem disease has traditionally been treated with systemic therapy. The LCH-1 clinical trial compared the effectiveness of vinblastine versus etoposide (in combination with a single dose of methylprednisolone). The vinblastine- and etoposide-based regimens were found to be equivalent with regard to disease response (58% vs. 65%, respectively), reactivation (61% vs. 55%), toxicity (47% vs. 58%), and survival (76% vs. 83%), as well as in prevention of disease-related permanent consequences such as diabetes insipidus, endocrinopathies (e.g. growth hormone deficiencies), orthopedic problems, hearing impairment, liver and lung failure, and CNS disease.

Small numbers of patients with reactivation of LCH have benefited from etanercept, cyclosporine or 2-chlorodeoxyadenosine (2-CdA), and a recent trial of 2-CdA plus cytosine arabinoside (ara-C) also showed efficacy, albeit with significant morbidity. Imatinib mesylate was also reportedly beneficial in a case of multisystem LCH involving the brain which was unresponsive to radiation. For those with the most severe disease, hematopoietic stem cell, liver or lung transplantation may be required.

The prognosis of patients with LCH varies dramatically. A high mortality rate is associated with multisystem disease, especially in children less than 2 years of age, and in any patient with multiorgan disease if the hematopoietic system, liver, lungs or spleen is involved. Even with aggressive treatment, mortality in this group of patients ranges from 35% to 55%. Patients not falling into this category tend to do better. Nevertheless, progression or persistence of disease is common.

Letterer-Siwe Disease—Letterer-Siwe disease is the acute diffuse form of LCH. It is a multisystem disease that nearly always develops prior to age 2 years, commonly presenting in children less than 1 year of age. Cutaneous involvement occurs in most patients as 1-2 mm pink to skin-colored papules, pustules and/or vesicles in the scalp, flexural areas of the neck, axilla and perineum, and on the trunk. Scale and crust with secondary impetiginization are common changes, as is the development of petechiae and purpura. The lesions tend to coalesce and become tender, especially when fissures develop in intertriginous zones. almoplantar and nail involvement can occur, as can soft tissue nodules. The eruption is most often confused with seborrheic dermatitis, various forms of diaper dermatitis or intertrigo, arthropod bites (including scabies), and varicella. During the course of the disease, many organs can become infiltrated by clonal LCH cells. However, only if the key functions of the organ are affected is such involvement of prognostic significance. Lung, liver, lymph node, and bone involvement commonly occur at some point during the illness. Osteolytic bone lesions are painful, usually multiple, and most frequently affect the cranium. Occasionally, the hematopoietic system can be involved, with thrombocytopenia and anemia portending a poor prognosis.

Hand-Schüller-Christian Disease—Classically, Hand-Schüller-Christian disease represents the triad of diabetes insipidus, bone lesions and exophthalmos. These patients tend to have a chronic progressive course. For most, Hand-Schüller-Christian disease begins between the ages of 2 and 6 years. Patients with the complete triad are rare, as exophthalmos is uncommon and often a late finding. Approximately 30% of patients develop skin or mucous membrane lesions. While early cutaneous lesions are similar to those seen in Letterer-Siwe disease, older lesions can become xanthomatous. Ulcerative nodules may develop in the oral and genital areas, with premature loss of teeth possible secondary to gingival lesions.

At least 80% of patients with Hand-Schüler-Christian disease develop bone lesions, the cranium being preferentially involved. Chronic otitis media occurs commonly in these patients and in patients with all forms of LCH. Diabetes insipidus, secondary to infiltration of the posterior pituitary by LCH cells, develops in approximately 30% of patients and is more common in those patients with cranial bone involvement. The chances of reversing the diabetes insipidus with radiation or chemotherapy are remote once symptoms develop. However, symptomatic treatment with vasopressin has been found to be effective in treating the diabetes insipdus.

Eosinophilic Granuloma—Eosinophilic granuloma is a localized variant of LCH that generally affects older children, boys more than girls. Skin and mucous membrane lesions are rare, with a single asymptomatic granulomatous lesion of the bone the most common manifestation. The cranium is most frequently affected, although lesions can also develop within the ribs, vertebrae, pelvis, scapulae, and long bones. A spontaneous fracture or otitis media may be the first sign of disease.

Hashimoto-Pritzker Syndrome—Congenital self-healing reticulohistiocytosis (Hashimoto-Pritzker disease or syndrome) is a variant of LCH which is generally limited to the skin and rapidly self-healing. It presents at birth or in the first few days of life with a characteristic eruption of widespread red to purplish-brown papulonodules. After several weeks, the lesions crust and involute. Solitary papules or nodules (often eroded or ulcerated) and disseminated vesicular eruptions have also been observed. Mucous membrane lesions are rare, although systemic involvement has been reported. While congenital self-healing reticulohistiocytosis is considered a benign, self-resolving disorder, its relationship to other LCH variants suggests a cautious approach with respect to prognosis.

Non-Langerhans Cell Histiocytosis (non-LCH)—As used herein, "non-Langerhans cell histiocytosis (non-LCH)" refers to the non-X histiocytoses. Non-X histiocytoses are divided clinically into three groups: those involving primarily or only the skin (e.g., JXG); those that affect the skin but have a major systemic component (e.g., Erdheim-Chester disease); and those that are primarily a systemic disease with occasional skin lesions as a part of the disease (e.g., sinus histiocytosis with massive lymphadenopathy, SHML). At any level of differentiation or appearance of the histiocyte there may be a disease in any category. Conceptually, this allows one to think of the skin-predominant (e.g., JXG) group of non-X histiocytoses as lying along a spectrum: benign cephalic histiocytosis (BCH), JXG, Erdheim-Chester disease, generalized eruptive histiocytosis, xanthoma disseminatum, and progressive nodular histiocytosis. Most diseases at the beginning of the spectrum are localized benign disorders. As one progresses through the diseases they tend to become more generalized but are still benign, and at the end of the spectrum lie diseases that are less likely to involute and may have visceral involvement. In any of these diseases, many morphologies of the histiocyte may be seen.

Benign Cephalic Histiocytosis (BCH)—As used herein, "benign cephalic histiocytosis" (BCH) refers to a rare skin condition typically seen in young children between a few months of age up to several years old. The disease begins initially on the head in virtually all cases, often the cheeks, eyelids, forehead, and ears. Lesions may later appear on the neck and upper trunk, and less commonly more caudad. Occasionally, they can be more generalized in distribution. There are nearly always multiple lesions, but often few in number (5-20), although they can number more than 100. Individual lesions are slightly raised, reddish-yellow papules, 2-4 mm in diameter. Lesions may coalesce to give a reticulate appearance. The lesions cause no symptoms. The mucosa and viscera are not involved. Lesions spontaneously involute over 2-8 years, leaving behind hyperpigmented macules. Some cases of BCH have evolved to become JXGs, and one patient later developed generalized eruptive histiocytoma many years after the involution of BCH. This supports the concept outlined above that these conditions may lie along a spectrum and all derive from the same cell type, a dermal dendritic cell. Histologically, there is a diffuse dermal infiltration of monomorphous macrophages, which stain positively for CD68 and factor XIIIa and negatively with S100 and CD1a.

Juvenile Xanthogranuloma" (JXG)—As used herein, "juvenile xanthogranuloma" (JXG) refers to the most common non-LCH. About ⅓ of lesions are congenital and the majority of lesions are diagnosed within the first year of life, but can occur in adulthood. Most lesions are solitary, but they can be multiple. Typically, a JXG begins as a well-demarcated, round to oval papule or nodule and appears pink to red with a yellow tinge, becoming yellow-tan-brown over time. Lesions appear histologically as nonencapsulated but circumscribed proliferations in the upper and mid-reticular dermis, and may extend more deeply into the subcutaneous tissue or abut directly on the epidermis with no Grenz zone. Epidermotropism does not occur. Classically, it has been proposed that the histopathology varies in accordance with the age of the lesion. Very early lesions are composed of mononuclear cells with abundant amphophilic cytoplasm that is poorly lipidized or vacuolated. Later, the cells become more vacuolated and multinucleated forms appear. In mature lesions, foam cells, multinucleated foam cells (Touton giant cells), and foreign-body giant cells are present. Touton giant cells are characteristic of JXG but not specific for it. The inflammatory infiltrate consists of lymphocytes, eosinophils, and neutrophils, and lacks plasma cells. Fibrosis occurs in the older lesions. The cells of JXG of all anatomic locations stain with factor XIIIa, vimentin, fascia, MS-1, and CD68, not with CD1, 5100, or other specific markers for Langerhans cells.

Several atypical presentations of JXG have been described. Extracutaneous JXG is uncommon and occurs as visceral involvement, including but not limited to ocular, sinus, lung, liver involvement, in association with either multiple cutaneous lesions or a solitary extracutaneous lesion. Rarely, the burden of visceral JXGs may be so great that the patient's life is threatened. These cases have been called "disseminated JXG," "systemic JXG," or "systemic xanthogranuloma." In 25% of these cases, no skin lesions are found. Progressive central nervous system (CNS), liver, or bone marrow involvement usually mandates aggressive therapy. These cases may simulate hemophagocytic lymphohistiocytosis syndrome. Locally aggressive tumors may be radiated. Systemic steroids, chemotherapy, and even liver or bone marrow transplantation may be required. Even more rarely, a visceral lesion may behave malignantly, spreading to previously unaffected organs and killing the patient. JXGs have been reported in association with neurofibromatosis (NF-1) and juvenile myelomonocytic leukemia (JMML). Patients with NF-1 and JXG are 20-32 times more likely to develop JMML.

Treatment for most cases of JXG is observation. By age 6 most lesions have resolved, often leaving normal or only slightly hyperpigmented skin. In adults spontaneous involution is slower, and local removal with surgery or $CO_2$ laser may be considered. It is noteworthy that the patterns of involvement by JXG and LCH are similar, with childhood onset and primary cutaneous involvement; when visceral disease occurs, the liver, bone, and lungs are commonly involved. Without histologic confirmation, isolated JXG of the bone would be most likely diagnosed as isolated LCH, a much more common condition. These clinical similarities between JXG and LCH may be explained by the fact that both diseases are caused by antigen-presenting dendritic cells. JXG is a proliferation of dermal dendrocytes and LCH is a proliferation of Langerhans cells. Clinical features favoring JXG include lack of crusting or scale and the distribution and uniformity of size of lesions. Histologic evaluation is definitive in difficult cases, since JXGs are negative for the Langerhans cell marker CD1. Unlike LCH, JXGs are usually negative for S100, although a few S100-positive JXGs have been reported.

Xanthoma Disseminatum—As used herein, "xanthoma disseminatum" (XD) refers to a very rare, potentially progressive non-LCH that preferentially affects males in childhood or young adulthood. It is characterized by the insidious onset of small, yellowish-red to brown papules and nodules that are discrete and disseminated. They characteristically involve the eyelids and flexural areas of the axillary and inguinal folds, and the antecubital and popliteal fossae. Over years the lesions increase in number, forming coalescent xanthomatous plaques and nodules. About 30-50% of cases have mucous membrane involvement, most commonly of the oropharynx (causing dysphagia), larynx (causing dysphonia and airway obstruction), and conjunctiva and cornea (causing blindness). Diabetes insipidus, usually transient, occurs in 40%. CNS involvement, with epilepsy, hydrocephalus, and ataxia, can occur. Synovitis and osteolytic bone lesions have been described. In some cases, the disease may spontaneously involute. The serum lipids are abnormal in 20% of cases, which may lead to confusion with hyperlipidemic xanthomatosis. Histologic examination of early lesions shows surprisingly nonfoamy, scalloped macrophages. Later lesions show xanthoma cells, Touton giant cells, and frequently a mild inflammatory cell infiltrate of lymphocytes, plasma cells, and neutrophils. The macrophages stain with CD68 and factor XIIIa.

Disseminated xanthosiderohistiocytosis is a variant of XD in which there is a keloidal consistency to the lesions; they have annular borders, a cephalad distribution, and extensive iron and lipid deposition in the macrophages and connective tissue. Progressive XD can produce considerable morbidity and can even be fatal. Therefore, aggressive therapy may be indicated. Systemic steroids have led to improvement in one case. In a patient with XD and dyslipidemia, the combination of rosiglitazone, simvastatin, and acipimox led to partial remission and stabilization of mucosal and osseous disease. Cyclophosphamide has led to dramatic improvement in two of three patients so treated.

Necrobiotic Xanthogranuloma—As used herein, "necrobiotic xanthogranuloma" refers to a disease with prominent skin findings. The cause is unknown and disease can be progressive. The most common site affected is the periorbital area (65-80% of cases). Multicentric involvement is typical. Characteristic skin lesions are yellow (xanthomatous) plaques and nodules. Periorbitally, they may be mistaken for xanthelasma, but they are deep, firm, and indurated, and may extend into the orbit. The trunk and proximal extremities may have orange-red plaques that have an active red border and an atrophic center with superficial telangiectasias. These plaques may grow to 25 cm in diameter. The skin lesions ulcerate in 50% of cases, leading to atrophic scarring. Acral nodules may also occur, some localized solely to the subcutaneous tissue. Extracutaneous involvement most commonly affects the eyes. Patients may complain of burning, itching, or pain around or in the eyes. Diplopia and inflammation in various compartments of the eye can occur, including conjunctivitis, keratitis, scleritis, uveitis, iritis, ectropion, or proptosis. Ulceration and scarring of the plaques and distortion of the eye may lead to visual occlusion. Blindness may result. Lymphadenopathy, hepatosplenomegaly, and mucosal, myocardial, and pulmonary lesions may occur. There is a monoclonal IgG (usually κ) paraproteinemia in 80% of cases, and rarely an IgA paraproteinemia (one patient had both). Thrombocytopenia, neutrophilia, neutropenia, and eosinophilia may be present. The bone marrow may show leukopenia, plasmacytosis (25-50% of patients), or frank myeloma (10-20% of patients). In some cases a myelodysplastic syndrome may be present or develop (chronic lymphocytic lymphoma, Hodgkin or non-Hodgkin lymphoma). The necrobiotic xanthogranuloma predates the development of the myeloma or myelodysplastic syndrome by an average of 2.5 years. Histologically, there are extensive zones of degenerated collagen surrounded by palisaded macrophages. These macrophages are of various forms—foamy, Touton cells, epithelioid, and giant cells, sometimes with more than 50 nuclei. Atypical multinucleated giant cells with multiple nuclei clustered at one end of the cell (polarized nuclei) are seen in 80% or more of cases. The process extends into the fat, obliterating fat lobules. Cholesterol clefts and extracellular lipid deposits are prominent. Within this process is a perivascular and interstitial infiltrate of lymphocytes and plasma cells. Lymphoid follicles are present. In the skin, the lymphoid aggregates are polytypic. The histologic differential diagnosis includes necrobiosis lipoidica and other histiocytoses. Necrobiotic xanthogranuloma has more atypical and Touton giant cells, lymphoid nodules, and cholesterol clefts.

Current treatment is usually directed at the paraprotein or underlying malignancy and consists of systemic corticosteroids, alkylating agents (including chlorambucil, cyclophosphamide, and melphalan), plasmapheresis, or local radiation therapy (for eye lesions). High dose intravenous immunoglobin (0.5 g/kg/d for 4 consecutive days 2 g/kg total) at 4 week intervals, IFN-α2b, 3-6 MU three times a week, in combination with systemic corticosteroids, and pulse cytoxan with dexamethasone, have both been reported to lead to improvement. Simple excision is an option, but lesions may recur.

Generalized Eruptive Histiocytoma—As used herein, "generalized eruptive histiocytoma" (GEH) refers to a rare disease, usually presenting in young adulthood, characterized by widespread, erythematous, essentially symmetrical papules, particularly involving the trunk and proximal extremities, sparing the flexors, and rarely involving the mucous membranes (there is no visceral involvement); progressive development of new lesions, often in crops, over several years with eventual spontaneous involution to hyperpigmented macules; and a benign histologic picture of monomorphous, vacuolated macrophages.

Lesions appear in crops, and may be grouped or clustered. They are skin-colored, brown, or violaceous. GEH is rare in childhood. In adults and children, GEH may suddenly appear several weeks following a bacterial or viral illness; in adults it may be associated with underlying malignancy, usually leukemia or lymphoma. GEH is distinguished from xanthoma disseminatum by the lack of visceral disease, the benign course, and by the scalloped appearance of the macrophages in xanthoma disseminatum. Histologically, there is a dermal infiltrate of monomorphous vacuolated macrophages and mononuclear histiocytes. The GEH cells stain positively for vimentin, CD68, and usually factor XIIIa, and negatively for S100, and CD1a. The natural history of GEH is unpredictable, with complete resolution in some cases and persistence in others. Some cases have progressed to widespread xanthogranulomas, xanthoma disseminatum, or progressive nodular histiocytosis. In childhood, no treatment may be required. In adulthood, treatment with PUVA or isotretinoin may be considered.

Progressive Nodular Histiocytoma—As used herein, "progressive nodular histiocytoma" refers to a variant characterized by a widespread eruption of hundreds of yellow-brown, 2-10 mm papules and deeper, larger subcutaneous nodules. Conjunctival, oral, and laryngeal lesions may occur. The face typically is heavily involved with numerous coalescent lesions, which may result in a leonine appearance. New lesions progressively occur, and ulceration is common. Occasionally, bleeding may occur within the subcutaneous nodules, resulting in marked pain. Lesions of progressive nodular histiocytoma histologically show features typical of xanthogranuloma, and some authors suggest that this entity and JXG may represent a variation of the same process. Current treatment for this condition is difficult, and includes excision of large or symptomatic lesions, chemotherapy with vinblastine, and electron beam therapy.

Indeterminate Cell Histiocytosis—As used herein, "indeterminate cell histiocytosis" (ICH) refers to rare disorders characterized by lesions that are composed of cells that immunophenotypically stain as Langerhans cells but lack Birbeck granules. Since electron microscopy is rarely employed, it is difficult to use this criterion to establish the diagnosis of a disorder. Langerin immunostaining might be substituted. S100 staining is variable in the various non-Langerhans cell histiocytoses (NLCH), making S100 positivity a soft criterion to use. In addition, reactive conditions are associated with tissue infiltration by S100-positive cells. Indeterminate cells may be found as a minor component of the dermal infiltrate in nodular scabies and rarely following pityriasis rosea. Both children and adults are affected by ICH, with males outnumbering females. Solitary and multiple lesions may occur, and the color of lesions varies from yellow to red-brown. Lesions may be papules, plaques, or nodules from 3 mm to 10 cm in size. These clinical features are not specific, and resemble the papular lesions seen in many forms of NLCH. Conjunctival involvement has been reported. Solitary malignant tumors with similar immunohistochemistry have been described, clinically resembling atypical fibroxanthoma. Histologically, while the cells in these cases do stain with S100 and at times with CD1a, the staining is never as intense as in Langerhans cells. ICH seems to have a benign course in the vast majority of cases, and no therapy is required. Broad-band UVB, PUVA, and total skin electron beam have each been reported to be effective in a limited number of cases with severe skin involvement. Many cases have been treated with numerous chemotherapeutic agents similar to those used for LCH, including cyclophosphamide, etoposide, vinblastine, systemic corticosteroids, and 2-chlorodeoxyadenosine, but therapeutic response has been equivocal. Acute myelogenous leukemia has followed some of these courses of chemotherapy. Solitary lesions with malignant histology is managed with surgical excision ensuring adequate margins. The utility of adjunctive therapy and sentinel lymph node sampling is not known.

Multicentric Reticulohistiocytosis—As used herein, "multicentric reticulohistiocytosis" refers to a rare systemic disorder of unknown cause. It is characterized by cutaneous lesions and a destructive arthritis, and is seen almost exclusively in adults, with rare reports of pediatric disease. The skin lesions present as firm red-brown papules, most often distributed on the hands, fingers, lips, ears, and nose. Facial disfigurement may occur, with cartilaginous destruction and the appearance of a leonine facies. The "coral bead" sign refers to the presence of a chain of papules along the cuticle. Nodular lesions on the arms, elbows, and knees may occur and at times resemble rheumatoid nodules. Mucous membrane involvement may occur in up to one-half of patients. They most often present on the lips, buccal mucosa, nasal septum, tongue, palate, and gingivae. Joint involvement is the presenting sign in more than half of patients and is highly destructive. It may involve any joint, especially the interphalangeal joints, and co-existing synovitis is common. Shortening of the digits may occur with a "telescopic" or "opera-glass" deformity. Rheumatoid arthritis may be mistakenly diagnosed in some patients. Microscopic examination of skin, bone, or synovial tissue reveals a characteristic histiocytic process, with multinucleated giant cells and a "ground-glass" appearance. Visceral involvement may include pleural effusion, pericarditis, heart failure, salivary gland enlargement, muscle weakness, lymphadenopathy, and gastric ulcer. Multicentric reticulohistiocytosis may regress spontaneously over 6-8 years, but for many patients the articular destruction results in permanent joint deformities. The response of this disorder to therapy is frequently disappointing, with current treatments including non-steroidal antiinflammatory agents, corticosteroids, cyclophosphamide, chlorambucil, methotrexate, hydroxychloroquine, and interferon.

Sinus Histiocytosis with Massive Lymphadenopathy—As used herein, "sinus histiocytosis with massive lymphadenopathy" (SHML) refers to a rare disorder of reactive proliferation of histiocytes in the sinuses of lymph nodes. It occurs primarily in children, who present with massive lymphadenopathy, especially cervical. Extranodal involvement may occur, and when it does, the skin is one of the more common organs to be involved. Papules and nodules are the most common skin lesions, and purely cutaneous SHML may occasionally occur. The lesions often involute spontaneously. There are isolated reports of patients with both SHML and lymphoma.

Hypertrophic Scars—As used herein, "hypertophic scars" refers to a form of abnormal wound healing characterized by local fibroblast proliferation and excessive collagen production in response to cutaneous injury. Compared to normal skin and normal scars, both hypertrophic scars and keloids have increased cellularity, vascularity and connective tissue. Hypertrophic scars are raised and confined to the wound margin, that is, in contrast to keloids, they remain confined to the site of the original injury. Sometimes hypertrophic scars improve spontaneously and tend to have a good response to treatment.

Both transforming growth factor (TGF)-β and platelet-derived growth factor (PDGF) have been shown to play an integral role in wound healing. For example, the majority of cells involved in wound healing express TGF-β in an initially inactive form (which becomes active following its release from the latency associated protein) that strongly promotes the chemotaxis of fibroblasts to the site of injury. In hypertrophic scars, there is an increase in both the number of fibroblasts and density of collagen fibers within the dermis. The orientation of both the cells, which are spindle-shaped, and the collagen becomes parallel to the skin surface. Dermal blood vessels are vertically oriented (i.e., perpendicular to the skin surface), and there may be a sparse perivascular inflammatory infiltrate. Elastic tissue is diminished or absent. Occasionally, immunohistochemical stains are also employed, such as the α-smooth muscle actin (α-SMA) stain to identify myofibroblasts. In one study, nodules of α-SMA-positive cells were observed only in hypertrophic scars.

Keloids—As used herein, a "keloid" or "keloidal scar" refers to a firm, irregularly shaped, fibrous, hyperpigmented, pink or red excrescence. The growth usually arises as the result of a cut, laceration, burn, or, less often, an acne pustule on the chest or upper back, or other injury, and spreads beyond the limits of the original injury, often sending out clawlike (cheloid) prolongations. The overlying epidermis is smooth, glossy, and thinned from pressure. The early, growing lesion is red and tender, and has the consistency of rubber. It is often surrounded by an erythematous halo, and the keloid may be telangiectatic. Lesions may be tender, painful, and pruritic, and may rarely ulcerate or develop draining sinus tracts. Keloids may be distinguished from hypertrophic scars by their clawlike projections and their lack of spontaneous improvement over a period of months.

In keloidal tissue, TGF-β, which is known to play a critical role in fibroblast proliferation and collagen production, is overproduced and poorly regulated via autocrine signaling pathways. At the same time, keloidal fibroblasts have increased expression of growth factor receptors, including for TGF-β and PDGF, and therefore respond more intensely to these growth factors. Decreased production of molecules that promote matrix breakdown (e.g., matrix metalloproteinases [MMPs]) may also be occurring within keloids. Lastly, in comparison to normal dermal fibroblasts, keloidal fibroblasts exhibit a reduced rate of apoptosis.

Histologically, a keloid is a dense and sharply defined nodular growth of myofibroblasts and collagen with a whorl-like arrangement resembling hypertrophic scar. Centrally, thick hyalinized bundles of collagen are present and distinguish keloids from hypertrophic scars. There is a paucity of elastic tissue, just as in a scar. By pressure, the tumor causes thinning of the normal papillary dermis and atrophy of adjacent appendages, which it pushes aside. Mucopolysaccharides are increased, and often there are numerous mast cells.

Current initial treatment is usually by means of intralesional injection of triamcinolone suspension alone or in combination with 5-fluorouracil (5-FU). Flattening and cessation of itching are reliably achieved by this approach, and may sometimes even be achieved with topical corticosteroids. The lesions are never made narrower, however, and hyperpigmentation generally persists. Transforming growth factor (TGF)-β is known to be involved in keloid formation, and triamcinolone acetonide-induced decreases in cellular proliferation and collagen production are associated with a statistically significant decrease in the level of TGF-β1 in both normal and keloid fibroblast cell lines. Other approaches to treatment include flashlamp pulsed dye laser treatment, which is also associated with reduced expression of TGF-β1. Cryosurgery (including contact, intralesional needle cryoprobe, and spray cryosurgery), intralesional 5-FU, intralesional etanercept, and calcium channel-blockers have some demonstrated efficacy in the treatment of keloids.

Proteus Syndrome—As used herein, "Proteus syndrome" refers to a rare and sporadic disorder characterized by postnatal overgrowth of multiple tissues. This overgrowth may involve the skin and subcutis, connective tissues, central nervous system, and viscera. The involvement characteristically occurs in a patchy (mosaic) and asymmetric pattern. Cutaneous findings are present in approximately 40 percent of neonates and include capillary, lymphatic, or venous malformations, epidermal nevi, connective tissue nevi, lipomas, and café au lait macules. The vascular malformations are usually extensive, covering a large portion of the body, and may be associated with visceral vascular malformations. Overgrowth is evident at birth in approximately 20 percent of cases and is asymmetric, disproportionate, and progressive. It may involve many tissues including bone, cartilage, muscle, and connective tissue.

The etiology of Proteus syndrome is thought to be due to mutations in the AKT1 gene, although there are some reports of a potential association with mutations in the tumor suppressor gene PTEN. Cutaneous manifestations of Proteus syndrome include connective tissue hamartomas, which primarily involve the palms and soles, resulting in cerebriform hyperplasia. Lipomas and extensive fatty hyperplasia may be found in the subcutaneous tissues as well as more diffusely, at times involving body cavities, muscles, and limbs, and regional absence of fat may also occur. Epidermal nevi are common. A variety of cutaneous and subcutaneous vascular malformations may occur, including capillary, venous, and lymphatic malformations. Patchy hypoplasia of the dermis may occur, resulting in prominent cutaneous venous structures.

PTEN Hamartoma Tumor Syndromes—As used herein, "PTEN hamartoma tumor syndromes" (PHTS) refers to a group of familial syndromes, which includes Cowden syndrome and Bannayan-Riley-Ruvalcaba syndrome (BRRS). Germline mutations in the phosphatase and tensin homolog (PTEN) gene have been described in a variety of rare syndromes with different clinical presentations that are collectively known as PTEN hamartoma tumor syndromes. The defining clinical feature of PHTS is the presence of hamartomatous tumors, which are disorganized growths of native cells in native tissues. PHTS is inherited in an autosomal dominant fashion. Cowden syndrome is associated with a high risk for the development of cutaneous hamartomas and internal malignancies such as breast, thyroid and endometrial carcinoma. BRRS is an autosomal dominant disorder characterized by macrocephaly, developmental delay, and penile lentigines. In both of these syndromes, associated vascular malformations are frequently described and usually consist of high flow, intramuscular vascular anomalies associated with increased adipose tissue. These vascular malformations have been found to be quite specific to PTEN hamartoma tumor syndromes and should prompt investigation, workup and continued monitoring for early-onset malignancies in suspected cases.

Cowden Syndrome—As used herein, "Cowden syndrome" (also known as Cowden disease or multiple hamartoma syndrome) is the best-described phenotype within PHTS. Besides multiple hamartomas in a variety of tissues, patients have characteristic dermatologic manifestations such as trichilemmomas, oral fibromas, and punctate palmoplantar keratoses, and an increased risk of breast, endometrial, thyroid, kidney and colorectal cancers. The range of clinical manifestations of Cowden syndrome includes hamartomatous tumors in multiple organ systems, both mucocutaneous and extracutaneous, and an increased risk for malignancy (including second malignant neoplasms. Skin and oral findings are distinctive and common manifestations of Cowden syndrome, and they are often the initial finding that leads to the diagnosis. Although commonly noticed in the second decade of life, the age of onset may vary from 4 to 75 years. The common lesions are trichilemmomas, acral keratoses, and facial papules/oral papillomas.

Trichilemmomas are hamartomatous tumors of the outer root sheath of the hair follicle or other skin appendages that occur on the face and neck of patients with Cowden syndrome. Trichilemmoma is a clinically significant sign of Cowden syndrome when seen in multiplicity (three or more). They present as wart-like, skin-colored papules with slightly rough surfaces; histologically, the lesions contain large glycogen-rich cells. Clinically, trichilemmomas are indistinguishable from trichoepitheliomas and other benign follicular tumors affecting the pilosebaceous unit, including fibrofolliculomas and trichodiscomas (which are characteristic lesions of Birt-Hogg-Dubé syndrome).

Bannayan-Riley-Ruvalcaba Syndrome—As used herein, "Bannayan-Riley-Ruvalcaba syndrome" (BRRS, previously referred to as Ruvalcaba-Myhre syndrome, Ruvalcaba-Myhre-Smith syndrome, Riley-Smith syndrome, Bannayan syndrome, or Bannayan-Zonana syndrome) is a rare autosomal dominant disorder that is caused by germline phosphatase and tensin homolog (PTEN) mutations. PTEN mutations are present in 55 to 60 percent of patients with a clinical diagnosis. Clinical manifestations arise early in childhood, one aspect that can be different from Cowden syndrome. Evaluation is often started in the first few years of life, with a reported median age of diagnosis as young as five years. Widely noted clinical findings include macrocephaly (at least two standard deviations above the mean), penile lentigines (a very characteristic marker of the disease), GI tract hamartomatous polyps, lipomas, vascular anomalies including arteriovenous shunts and fistulae, intramuscular lesions with a mixture of adipose tissue, fibrous tissue, and abnormal vessels (labeled a PTEN hamartoma of soft tissue, Hashimoto thyroiditis and other thyroid disorders including thyroid cancer, mild-to-severe developmental delay or deficiency, proximal muscle myopathy, high palate, joint hypermobility, and eye abnormalities such as downslanting palpebral fissures, strabismus, and amblyopia.

Keratoderma—As used herein, "keratoderma" refers to any of a diverse group of hereditary and acquired disorders characterized by hyperkeratosis of the skin on the palms and soles (palmoplantar keratodermas (PPKs)). Included within this group of disorders are Unna-Thost type: non-epidermolytic PPK; Vörner type: epidermolytic PPK; Meleda type: Mal de Meleda; Greither type: transgrediens and progrediens PPK; Gamborg-Nielsen (Norrbotten) type; Sybert type; Vohwinkel syndrome: mutilating PPK; PPK with sensorineural deafness due to mitochondrial or GJB2 gene defect; Bart-Pumphrey syndrome: knuckle pads, leukonychia, and sensorineural deafness; Huriez syndrome: PPK with scleroatrophy; PPK with sex reversal and squamous cell carcinoma; hidrotic ectodermal dysplasia: Clouston syndrome; Olmsted syndrome: mutilating PPK with periorificial plaques; Papillon-Lefèvre syndrome: PPK with periodontitis; Haim-Munk syndrome: PPK with periodontitis, arachnodactyly and acro-osteolysis; Naxos disease: diffuse PPK with woolly hair and arrhythmogenic cardiomyopathy; PPK striata/areata type: striate PPK, focal non-epidermolytic PPK, Wachters type, Brünauer-Fuhs-Siemens type; hereditary painful callosities: nummular epidermolytic PPK, focal epidermolytic PPK; Howel-Evans syndrome: non-epidermolytic PPK with carcinoma of the esophagus; Richner-Hanhart syndrome: oculocutaneous tyrosinemia; Carvajal syndrome: striate PPK with woolly hair and dilated cardiomyopathy; focal palmoplantar and gingival keratosis; punctate palmoplantar keratoderma: keratosis punctata palmaris et plantaris, Buschke-Fischer-Brauer type; acrokeratoelastoidosis; focal acral hyperkeratosis; porokeratosis punctata palmaris et plantaris; keratoderma climactericum; spiny keratoderma; keratoderma associated with hypothyroidism/myxedema; keratoderma associated with cancer; aquagenic PPK; drug-induced keratoderma (e.g. lithium, verapamil, venlafaxine, tegafur, imatinib, glucan, capecitabine); keratitis-ichthyosis-deafness (KID) syndrome; hystrix-like ichthyosis-deafness (HID) syndrome; erythrokeratodermia variabilis; progressive symmetric erythrokeratoderma; epidermolytic ichthyosis (bullous congenital ichthyosiform erythroderma); ichthyosis hystrix Curth-Macklin; congenital ichthyosiform erythroderma; lamellar ichthyosis; harlequin ichthyosis; Sjögren-Larsson syndrome; Refsum syndrome; CEDNIK (cerebral dysgenesis, neuropathy, ichthyosis and keratoderma) syndrome; MEDNIK (mental retardation, enteropathy, deafness, neuropathy, ichthyosis and keratoderma) syndrome; KLICK syndrome (keratosis linearis with ichthyosis congenita and sclerosing keratoderma); Netherton syndrome (rarely); ectodermal dysplasia with skin fragility; acantholytic ectodermal dysplasia; Schöpf-Schulz-Passarge syndrome: PPK with hidrocystomas, hypodontia and hypotrichosis; odonto-onycho-dermal dysplasia; ectodermal dysplasia-ectrodactyly-clefting (EEC) syndrome; cleft lip/palate ectodermal dysplasia; oculo-dento-digital dysplasia; Naegeli-Franceschetti-Jadassohn syndrome, dermatopathia pigmentosa reticularis; epidermolysis bullosa; Kindler syndrome; erythropoietic protoporphyria; familial pityriasis rubra pilaris; linear PPK associated with epidermal nevus; dyskeratosis congenita; Darier disease (typically punctate); Cowden disease (punctate); porokeratotic eccrine ostial and dermal duct nevus (PEODDN; porokeratotic adnexal ostial nevus); cardiofacio-cutaneous syndrome; HOPP (hypotrichosis, acro-osteolysis/onychogryphosis, palmoplantar keratoderma and periodontitis) syndrome; Cantu syndrome: hyperkeratosis-hyperpigmentation syndrome; and Cole disease: guttate hypopigmentation with punctate PPK. In certain embodiments, any one or more of the foregoing forms of keratoderma are excluded.

Acanthosis Nigricans—As used herein, "acanthosis nigricans" refers to a skin condition characterized by hyperpigmentation and velvet-textured plaques, which are symmetrically distributed. The regions affected may be the face, neck, axillae, external genitals, groin, inner aspects of the thighs, flexor and extensor surface of the elbows and knees, dorsal joints of the hands, umbilicus, and anus. With extensive involvement, lesions can be found on the areolae, conjunctiva, lips, and buccal mucosa, and around the umbilicus. Rarely, the involvement may be almost universal. The color of the patches is grayish, brownish, or black. The palms or soles may show thickening of the palmar skin with exaggeration of the dermatoglyphs. In severe cases a rugose hypertrophy occurs and can be a sign of malignancy. Small, papillomatous, nonpigmented lesions and pigmented macules may occasionally be found in the mucous membranes of the mouth, pharynx, and vagina. Acrochordons are a frequent accompaniment in the axillae and groin. There is a clear predisposition for certain racial groups to manifest acanthosis nigricans, with Native Americans most commonly affected, followed by African Americans and Hispanics, all above the rates in Caucasians.

The pathways that lead to acanthosis nigricans are not well understood. Abnormalities involving three types of tyrosine kinase receptors, insulin-like growth factor receptor-1 (IGFR1), fibroblast growth factor receptor (FGFR), and epidermal growth factor receptor (EGFR), have been proposed as potential contributing factors. The association of acanthosis nigricans with multiple disorders characterized by insulin resistance suggests that hyperinsulinemia plays a key role in the development of acanthosis nigricans. Elevated levels of insulin may stimulate keratinocyte and dermal fibroblast proliferation via interaction with IGFR1, resulting in the plaque-like lesions that typify the disorder. Other mechanisms may also be involved in acanthosis nigricans, particularly in cases in which insulin resistance is absent. As an example, mutations in certain FGFRs may contribute to acanthosis nigricans through the promotion of keratinocyte proliferation and survival. Activating mutations in FGFR3 have been linked to several inherited syndromes that present with acanthosis nigricans, including Crouzon syndrome, severe achondroplasia with developmental delay and acanthosis nigricans (SADDAN), thanatophoric dwarfism, and hypochondroplasia.

Transforming growth factor (TGF)-alpha, a cytokine that may exert proliferative effects via activation of EGFR, may also contribute to the development of malignancy-associated acanthosis nigricans. In support of this theory is a report of a patient in whom reduction of elevated serum TGF-alpha levels and amelioration of acanthosis nigricans followed the removal of a malignancy.

Hyperkeratosis and epidermal papillomatosis are the major pathologic features, and acanthosis is relatively mild. The hyperkeratosis is primarily responsible for the clinical finding of cutaneous hyperpigmentation; however, increased melanin in the basal layer of the epidermis also is sometimes detected. The dermis may demonstrate a mild infiltrate with lymphocytes, plasma cells and, occasionally, a few neutrophils. However, inflammation is not a prominent feature. Biopsies of mucosal lesions exhibit mild parakeratosis with epidermal hyperplasia and papillomatosis.

Treatment of the underlying cause, when feasible, is the preferred method of management, and obesity-related, drug-induced, and malignancy-associated acanthosis nigricans appear to frequently respond well to this intervention. In contrast, the likelihood for clinically significant improvement in acanthosis nigricans following the treatment of insulin resistant states is less certain. For patients in whom reversal of the underlying cause of acanthosis nigricans is impossible, in whom the degree of improvement is unsatisfactory, or who desire accelerated improvement in the cosmetic appearance of lesions, topical therapies that normalize epidermal proliferation, such as topical retinoids and topical vitamin D analogs, have been tried. Systemic retinoids have also been utilized for this indication, but are not indicated for the treatment of most patients.

Birt-Hogg-Dubé (BHD) Syndrome—As used herein, "Birt-Hogg-Dubé syndrome" or "BHD syndrome" refers to an autosomal dominant condition first described in 1977, characterized by benign skin hamartomas, most commonly located on the head and neck; pulmonary cysts and spontaneous pneumothorax; and an increased risk of renal cancer. BHD syndrome is caused by germline mutations in the folliculin gene (FLCN), which encodes the protein folliculin, a putative tumor suppressor gene whose function is still under investigation. The phenotype of Birt-Hogg-Dubé

(BHD) syndrome is highly heterogeneous within families and between families sharing the same folliculin (FLCN) mutation. No clear correlations have been identified between the type of FLCN mutation and the extent of skin involvement and lung or kidney manifestations. Some patients may develop cutaneous lesions only, while others may present with cutaneous lesions and pulmonary manifestations or cutaneous lesions and kidney tumors. In some patients, pulmonary cysts or renal tumors may be the only manifestation of the disease.

Fibrofolliculoma, a benign hamartoma of the hair follicle, is the hallmark skin finding of Birt-Hogg-Dubé (BHD) syndrome. Fibrofolliculomas are typically the earliest and most frequent manifestation of BHD syndrome. They begin to appear in the third decade of life in approximately 90 percent of patients and present as round, white-gray papules 1 to 4 mm in size, some of which show a dell in the center corresponding to the follicular opening. Lesions as large as 8 mm and cystic or comedonal lesions may also occur. The midface (cheeks, nose) is most densely affected, and the papules are also often most prominent at this location, particularly in fair-skinned individuals with a rosaceiform complexion. Lesions may develop anywhere on the head/neck, including the posterior ears. Isolated papules on the neck may be difficult to differentiate from acrochordons (skin tags) or small seborrheic keratoses. Affected patients will continue to slowly accumulate new lesions and experience enlargement of pre-existing lesions throughout life. However, some patients have only a small number of lesions by late adulthood, whereas others may develop hundreds, at times near confluent, in the head/neck area.

Other skin lesions initially described in BHD syndrome along with fibrofolliculomas include trichodiscomas and acrochordons. Trichodiscomas are clinically indistinguishable from fibrofolliculomas and may represent a histologic variant of the same tumor. Acrochordons (skin tags) are common in the general population, and their presence or absence is not helpful in making/excluding a diagnosis of BHD syndrome. Angiofibromas (also known as fibrous papules) may occasionally be seen in the setting of BHD syndrome but are also common in the general population.

Fibrofolliculomas and trichodiscomas are benign lesions that usually do not require treatment. However, some patients with numerous facial lesions may seek treatment because of cosmetic concerns. Destructive therapies, including shave removal, electrodessication with or without curettage, and carbon dioxide ($CO_2$) or erbium:yttrium aluminum garnet (Er:YAG) laser ablation, have been used in a few patients with good results, although recurrence is commonplace. In a randomized, split-face trial including 19 patients, topical rapamycin (sirolimus) 0.1% oral solution did not result in reduction in size or number of fibrofolliculoma lesions compared with placebo. Gijezen L M et al., *PLoS One* 9(6):e99071 (2014).

Cylindromas—Yet other skin lesions described in BHD syndrome include cylindromas (also known as turban tumors). These are benign neoplasms of either eccrine or apocrine origin, characterized by firm, rubbery, pink to bluish plaques and nodules. They may range in size from a few millimeters to several centimeters, and are located primarily on the scalp and occasionally the face, trunk, or extremities. Cylindromas may occur singly or in multiples, and occasionally coalesce to result in large mosaic tumors. Multiple lesions may occur as part of the autosomal dominant Brooke-Spiegler syndrome (with multiple trichoepitheliomas and occasionally other appendageal tumors. This disease has been mapped to 16q12-13, and mutations in the CYLD gene have been identified in families with this disorder. Cylindromas are almost invariably benign, although malignant transformation has been rarely reported. Current treatment consists of surgical excision, although $CO_2$ laser surgery has also been demonstrated useful.

Brooke-Spiegler Syndrome—As used herein, "Brooke-Spiegler syndrome" refers to a rare condition with a predisposition to develop cutaneous adnexal neoplasms, especially cylindromas, trichoepitheliomas and spiradenomas. Malignant transformation of cylindromas is rare. In such cases usually cylindrocarcinomas develop within these lesions. Brooke-Spiegler syndrome is caused by mutations in the CYLD gene.

Epidermal Nevi—As used herein, "epidermal nevi" refers to benign congenital lesions characterized by hyperplasia of epidermal or dermal structures. They are usually apparent at birth or become noticeable during early childhood, affect both sexes equally, and are known by several descriptive names, including nevus verrucosus, nevus unius lateris, and ichthyosis hystrix. In addition, epidermal nevi can be divided into non-organoid (keratinocytic) nevi and organoid epidermal nevi, such as nevus sebaceous or follicular nevi. Although the exact etiology of epidermal nevi is unknown, activating fibroblast growth factor receptor 3 (FGFR3) mutations have been demonstrated in some, as have mutations in the p110 α-subunit of PI3K (PIK3CA).

Keratinocytic epidermal nevi (frequently referred to simply as "epidermal nevi") may be slightly or darkly pigmented and unilateral or bilateral in distribution. They often favor the extremities, although they may occur anywhere on the cutaneous surface. Epidermal nevi are usually distributed in a mosaic pattern of alternating stripes of involved and uninvolved skin. This pattern is termed "Blaschko's lines" and occurs as a result of migration of skin cells during embryogenesis. Disorders that occur along Blaschko's lines usually reveal a linear pattern on the extremities and a wavy or arcuate pattern on the trunk. Although a single epidermal nevus is most common, multiple lesions may be present, sometimes in association with the "epidermal nevus syndrome" (see below). The localized form is often present at birth and presents as a tan to brown, velvety or verrucous (warty) papule or plaque. There may be a single lesion or multiple lesions, and a linear configuration is common. One subtype of epidermal nevus has been termed the acanthosis nigricans form of epidermal nevi, and it is characterized by a clinical and histologic resemblance to acanthosis nigricans.

Epidermal nevi may reveal a variety of histologic features. Importantly, those that reveal "epidermolytic hyperkeratosis," a distinct pattern of clumping of keratin filaments in the suprabasal cells of the epidermis, imply a mosaic disorder of keratin genes. These patients, especially when skin involvement is extensive, may transmit these mutations to offspring, resulting in a more widespread ichthyosiform condition termed "epidermolytic ichthyosis" (formerly "bullous congenital ichthyosiform erythroderma," and "epidermolytic hyperkeratosis"). These epidermal nevi may be clinically indistinguishable from other epidermal nevi.

Epidermal nevi are challenging to treat, given the observation that most superficial destructive therapies are followed by recurrence of the lesion(s). These superficial therapies have included cryotherapy with liquid nitrogen, dermabrasion, electrodessication, and laser ablation. $CO_2$ laser therapy may offer excellent results, but response to therapy is unpredictable. Staged $CO_2$ laser ablation has been used successfully, both with and without preceding surgical debulking. Topical therapies used with variable success include retinoids, 5-fluorouracil, steroids, and podophyllin, among others. Full-thickness surgical excision or deeper destructive procedures (such as deep dermabrasion) appear effective at removing these hamartomas, but are generally limited to smaller, more localized lesions. Since these lesions may continue to extend during childhood, surgical intervention is usually delayed until the full extent of the process is determined.

Inflammatory linear verrucous epidermal nevus (ILVEN) appears to be a unique variant of epidermal nevus that presents as a chronic pruritic process with erythematous, scaly, and verrucous papules that coalesce into linear plaques.

Nevus sebaceous of Jadassohn is a common congenital lesion that occurs mainly on the face and scalp. These lesions are usually solitary, and present as a well-circumscribed, hairless plaque. A developmental defect, they are generally present at birth, but may first be noted during early childhood and rarely in adult life. Although rare familial forms have been reported, these hamartomas tend to be sporadic. Multiple nevi sebaceous may occur in association with cerebral, ocular, and skeletal abnormalities as part of the epidermal nevus syndrome. This association has been termed Schimmelpenning syndrome.

An epidermal nevus is a congenital overgrowth of epidermal cells that is often due to a mosaic mutation, sometimes involving mutations in fibroblast growth factor receptor 3 (FGFR3). The mTOR complex is known to negatively regulate FGFR3. Hence, it is conceivable that topical mTOR inhibitor such as rapamycin would be effective in treating some epidermal nevi due to this direct pathway involvement and the favorable results of studies disclosed in the Examples herein.

Cutaneous Vascular Conditions

As used herein, a "cutaneous vascular condition" refers to a skin condition characterized by abnormal or undesirable proliferation of principally vascular structures or vascular tissue in skin. The skin condition characterized by abnormal or undesirable proliferation of principally vascular structures or vascular tissue in skin can be a cutaneous manifestation of a multisystemic or more general condition that is not confined to skin.

For purposes of this disclosure, to the extent that any cutaneous proliferative condition as defined herein is considered to be, or can be considered to be, a cutaneous vascular condition, such cutaneous proliferative condition is to be understood also to be included among cutaneous vascular conditions in accordance with the invention.

Cutaneous vascular conditions include, without limitation, PIK3CA-related overgrowth spectrum (PROS), venolymphatic malformations, acne, acne rosacea (including rhinophyma), periorifacial dermatitis (also known as perioral dermatitis), fibrous papules, acne vulgaris, cutaneous capillary malformation-arteriovenous malformation (CM-AVM) syndrome, and RASopathies, including neurofibromas.

In certain embodiments, the cutaneous vascular condition is venolymphatic malformations.

In certain embodiments, cutaneous vascular conditions exclude any one or more of facial angiofibromas in tuberous sclerosis, microcystic lymphatic malformations, and port wine stains.

Rapamycin has been reported to be effective in the treatment of several vascular conditions, namely port wine stains (PWS) in combination with laser, facial angiofibromas either alone or in combination with pulsed dye laser treatments, and other cutaneous features of Tuberous Sclerosis Complex. Animal studies and preliminary studies on normal human skin have demonstrated the effectiveness of rapamycin in inhibiting revascularization and hence, increasing the effectiveness of pulsed dye laser (PDL) treatments. Additionally, one case report demonstrated improved clinical outcome of a PWS in an adult treated with combined oral rapamycin and PDL. Also, an ongoing study (ClinicalTrials.gov Identifier: NCT00830466) is examining the effects of combined treatment of PWS with PDL and oral rapamycin.

Although adjuvant treatment with oral rapamycin may be effective, the alternative use of topical rapamycin could potentially provide similar results without the systemic side effects. Case reports and studies examining the use of topical rapamycin in the treatment of facial angiofibromas have demonstrated that topical use can be effective without systemic absorption or significant side effects (DeKlotz et al., *Arch Dermatol* 147: 1116-7 (2011)). Additionally, preliminary animal and human studies on normal skin have shown improved effectiveness of PDL when combined with topical rapamycin.

Additionally, mTOR inhibitors have shown promise as a systemic treatment of complex vascular malformations in children, including venolymphatic malformations. Overexpression of mTOR has been found in some vascular malformations. The phosphoinositide-3-kinase (PI3K)/Akt pathway, which is implicated in some vascular anomalies, is an upstream regulator/inducer of the mTOR complex. Therefore, the mechanism of sirolimus in treating vascular malformations may be by preventing the downstream effects of PIK3CA/AKT overexpression. Additionally, vascular endothelial growth factor (VEGF) likely plays a role. VEGF, a key regulator in angiogenesis and lymphangiogenesis, potentially both stimulates the mTOR pathway and downstream appears to be effected by mTOR, and mTOR inhibitors have been shown to decrease both the secretion of VEGF and the sensitivity of its receptors.

The components of the PI3K/AKT/mTOR pathway are known to interact with other pathways, including Ras/MAPK (Ras/mitogen-activated protein kinases) pathway. Capillary malformation-arteriovenous malformation (CM-AVM) syndrome presents with pink red-tan vascular macules and patches with or without internal AVM. CM-AVM is typically due to mutations in the RASA1 gene, which is in the GNAQ/RAS/MEK/ERK pathway. Although a different pathway, this is related to the mTOR pathway and additionally, clinically, CM-AVM is characterized by cutaneous capillary vascular malformations. Hence, inventor expects the cutaneous lesions in CM-AVM to improve with a topical mTOR inhibitor such as topical rapamycin, given its anti-angiogenesis effects and favorable results of studies disclosed in the Examples herein.

Additionally, other RASopathies (syndromes and diseases due to mutations in the RAS pathway) are expected to respond to treatment with an mTOR inhibitor (systemic or topical). Such conditions include but are not limited to autoimmune lymphoproliferative syndrome, cardiofaciocutaneous syndrome, hereditary gingival fibromatosis, neurofibromatosis type 1, Noonan syndrome, Costello syndrome, Legius syndrome, and Noonan syndrome with multiple lentigines. Additionally, the cutaneous lesions that characterize these conditions, including but not limited to neurofibromas, are similarly expected by the inventor to respond to treatment with systemic or topical mTOR inhibitors.

PIK3CA-Related Overgrowth Spectrum (PROS)—As used herein, "PIK3CA-related overgrowth spectrum" (PROS) refers to certain syndromes associated with various vascular anomalies. Somatic PIK3CA mutations are the most common cause of isolated lymphatic malformations and disorders in which lymphatic malformation is a component feature. Broadly speaking, these syndromes can be classified as syndromes associated with capillary malformations and syndromes associated with venous malformations. Syndromes associated with capillary malformations include Sturge-Weber syndrome, macrocephaly capillary malformation syndrome (megalencephaly capillary malformation polymicrogyria syndrome), Beckwith-Wiedemann syndrome, Nova syndrome, and phakomatosis pigmentovascularis (PPV). Syndromes associated with venous malformations include venous malformations cutaneous and mucosal (VMCM), glomuvenous malformations, blue rubber bleb nevus syndrome (Bean syndrome), Maffucci syndrome, cutis marmorata telangiectatica congenita, and capillary malformation-arteriovenous malformation. Gain-of-function mutations in PIK3CA lead to the activation of protein kinase B (AKT) and, ultimately, mammalian target of rapamycin (mTOR), with resultant cell proliferation and angiogenesis. Similar mutations have been discovered in entities such as congenital lipomatous overgrowth with vascular malformations, epidermal nevi, and skeletal anomalies (CLOVES) syndrome, fibro-adipose vascular anomaly (FAVA), and macrocephaly-capillary malformation (M-CM, MCAP) syndrome.

Most of these malformations are evident at birth or become apparent in infancy or early childhood. In some cases, the genetic basis for the syndrome is known.

Sturge-Weber Syndrome—The classic triad in Sturge-Weber syndrome (SWS) includes the association of a facial port-wine stain (PWS), invariably involving V1 (although it may be more extensive), ipsilateral eye abnormalities (choroidal vascular anomalies, increased ocular pressure, buphthalmos, and glaucoma), and leptomeningeal and brain abnormalities (leptomeningeal vascular malformation, calcifications, cerebral atrophy, enlarged choroid plexus, and developmental venous anomalies in the brain). [V1, V2, and V3 refer to areas served by the upper, middle, and lower facial sensory branches of the trigeminal nerve (i.e., cranial nerve V), respectively.] The risk of SWS with V1 PWS alone is variably reported but is approximately 10%. The risk increases to ≥25% with either bilateral V1 or concurrent V1, V2, and V3 involvement. Patients with V2 or V3 PWS alone without involvement of the V1 skin are not at risk for SWS. However, individual anatomic variations in the distribution of V1 and V2 at the internal or external canthus of the eye may pose difficulties in determining whether a port-wine stain involves V1, with its associated risk of SWS. The possibility of SWS should be considered in any infant with a PWS that includes the V1 distribution.

SWS can cause significant medical and ophthalmologic problems. Consequences of intracranial vascular anomalies include seizures, headaches (including migraines), spastic hemiparesis, visual field defects, cognitive impairment and behavioral disorders including attention deficit disorder. Transient ischemic attacks and strokes may also occur in some patients. An increased prevalence of growth hormone deficiency and hypothyroidism is described in patients with SWS, so at-risk individuals need to be assessed for these potential complications. Potential visual loss via acute or chronic glaucoma requires ongoing ophthalmologic follow-up throughout a patient's lifetime. Even an individual who has a V1 PWS without CNS findings should have periodic ophthalmologic evaluations throughout their lifetime.

The pathogenesis of SWS has recently been attributed to somatic activating mutations in GNAQ, the gene encoding guanine nucleotide-binding protein G(q) subunit alpha. The three mesectodermal tissues involved (the nasofrontal skin known as V1 skin, the ocular choroid, and the leptomeninges) have a common origin in the anterior neural primordium, and a somatic mutation arising during development has been hypothesized. Neuroimaging consisting of MRI with gadolinium enhancement may be helpful in making an early diagnosis, but can be normal in some cases. Early subtle changes on standard MRI can include an enlarged choroid plexus or a pattern of local accelerated myelination. Typical neuroimaging changes include visualization of the pial vascular malformation, cerebral atrophy, and calcifications of the leptomeninges, the abnormal cortex and the underlying white matter. Newer MRI modalities such as susceptibility-weighted imaging may prove useful in detecting abnormalities earlier in life. In most patients, the first seizures in SWS occur before 2 years of age but may arise later in life. The progressive nature of SWS has been demonstrated using functional neuroimaging tools, with hyperperfusion noted prior to the development of seizures, followed by hypoperfusion with decreased glucose utilization after the onset of seizures.

Macrocephaly Capillary Malformation Syndrome—Macrocephaly capillary malformation syndrome (MCM/MCAP) was formerly known as macrocephaly CMTC. The most commonly associated vascular anomalies are a persistent nevus simplex or typical capillary malformation/port wine stain. MCM/MCAP is associated with megalencephaly, developmental delay, brain and body asymmetry, capillary malformations, digital anomalies (syndactyly, polydactyly), and brain malformations; characteristically, polymicrogyria. Other features include seizures, developmental delay, hydrocephalus, and joint laxity. Recently, the genetic basis for this condition has been identified. Affected individuals have been reported to harbor mutations in the AKT3, PIK3CA or PIK3R2 genes. MCM/MCAP is a heterogeneous overgrowth syndrome, and most commonly patients present with macrocephaly and cutaneous capillary malformations. The associated capillary stain is most commonly located on the central face (philtrum and glabella) but can be seen on any area of the body.

Beckwith-Wiedemann Syndrome—Beckwith-Wiedemann syndrome (BWS) is a pediatric overgrowth disorder that carries an increased risk for malignancy, specifically Wilms tumor. BWS can present antenatally with visceromegaly on prenatal ultrasonography. It is associated with persistent nevus simplex or capillary malformation of the mid-forehead. Other findings include overgrowth of tissues and organs, macroglossia, and abdominal wall defects, usually omphalocele. High birthweight, hemihypertrophy, and neonatal hypoglycemia are also reported. Intelligence is usually not impaired.

Nova Syndrome—Nova syndrome is a familial disorder in which a congenital glabellar capillary stain occurs in association with neurologic malformations, including Dandy-Walker malformation, hydrocephalus, cerebellar vermis agenesis, and mega cisterna magna.

Phakomatosis pigmentovascularis—As used herein, "phakomatosis pigmentovascularis" (PPV) refers to the association of cutaneous pigmentary and vascular anomalies. Five types with two subtypes per group are classically described. Capillary malformations are described in types I-IV and cutis marmorata telangiectatica congenita in type V.

The pigmentary anomalies include blue-gray macules/patches (dermal melanocytosis), nevus spilus and epidermal nevi which are darkly pigmented. Nevus anemicus is also reported. PPV has been described in association with other vascular anomalies including Klippel-Trenaunay syndrome and Sturge-Weber syndrome.

Venous Malformations Cutaneous and Mucosal (VMCM)—Somatic and familial venous malformations arise due to mutations in the Tie2 gene, a tyrosine kinase receptor involved in angiogenesis. In the familial VMCM syndrome, the malformations are typically small and superficial, located mainly in the skin and mucosa, though they can be found invading skeletal muscle and have been reported both in the GI tract and the brain. Since the lesions are usually small and asymptomatic, family members may be unaware of the syndrome, even though it is inherited in an autosomal dominant pattern. Lesions can be present early on and individuals can acquire more VMs with time. This is due to the mode of inheritance, whereby a second mutation within the Tie2 gene leads to the development of more lesions.

Glomuvenous Malformations—Familial glomuvenous malformations are usually inherited in an autosomal dominant manner, but can also be sporadic. Mutations in the glomulin gene have been identified in affected patients. GVM often resemble VM clinically. They can be small or large/segmental in their appearance. They are bluish to purple, cobblestoned in appearance and often painful on palpation. There is great heterogeneity among affected family members, which suggests that a single mutation in the glomulin gene is not enough to produce the lesion, thus as in VMCM, a second post-zygotic mutation in the unaffected allele is required for the lesion to develop.

Blue Rubber Bleb Nevus Syndrome—As used herein, "blue rubber bleb nevus syndrome" (BRBNS) refers to a rare congenital disorder in which patients present with multifocal venous malformations in the skin, soft tissue, and gastrointestinal tract. The associated VMs are typically small black-blue papules and skin-colored subcutaneous nodules that often involve the palms and soles. GI bleeding is a frequent clinical feature of this syndrome.

Maffuci Syndrome—As used herein, "Maffucci syndrome" (MS) refers to a rare sporadic syndrome characterized by vascular lesions of the skin and multiple bone tumors. This form of enchondromatosis is associated with spindle cell hemangioma, begins in childhood and worsens with maturity. Congenital forms occur and disease presents in 25% of cases by the first year of life. The skin lesions clinically resemble venous malformations, are nodular, develop slowly, and are rare in infancy. Although they have features of slow-flow venous anomalies—phleboliths, hypersignal on signal-enhanced $T_2$ sequences with MRI—histologic examination reveals a spindle cell hemangioma, in addition to malformed venous channels. Enchondromas are benign cartilage-forming tumors within the medullary cavity of the bone. These tumors are identical to those present in another form of multiple enchondromatosis, Ollier disease. They involve both the metaphyses and the diaphyses, and may cause bony distortion, fragility, and shortening of an affected limb. The hands and feet are involved in 90% of patients. Cranial enchondromas result in severe neuro-ophthalmologic consequences. Over time, enchondromas may develop malignant transformation. Somatic mosaic IDH1 and IDH2 mutations are associated with the lesions in both Ollier disease and MS.

Cutis Marmorata Telangiectatica Congenita—As used herein, "cutis marmorata telangiectatica congenita" (CMTC) refers to a form of vascular malformation with a distinctive reticulated pattern. Most cases are sporadic. A female predominance is reported in some cases series, while others show no difference in incidence among genders. CMTC can be confined to a small area, have a regional distribution, or more diffuse skin involvement. At birth, a reticulated purple network is noted. The skin is streaked with linear and patchy vascular lesions intermingled with telangiectasia. Within affected areas there are often focal areas of atrophy and/or ulceration, even during the neonatal period. These changes are often most prominent over the limbs. This conspicuous atrophic reticulate pattern differs from physiologic cutis marmorata, a normal finding in newborns, in that the pattern is coarse and less regular. CMTC may be associated with port-wine stains, which can become more apparent with maturity as the reticulate lesions fade. CMTC may improve with age, but rarely disappears completely with areas of atrophy often persisting. Ulcerations may continue to arise during infancy and childhood, particularly in areas overlying the joints, resulting in scaly areas of scarring.

Klippel-Trenaunay Syndrome—As used herein, "Klippel-Trenaunay syndrome" (KTS) refers to a complex congenital disorder that historically has been defined as the triad of capillary malformation, venous malformation, and limb overgrowth. In the past, a number of different conditions have been lumped together under the moniker of KTS, including Parkes Weber syndrome and diffuse capillary malformation with overgrowth (DCMO), but clearer descriptions of phenotype and emerging genotypic studies have helped in distinguishing these disorders. Most cases of KTS analyzed genomically were found to be caused by mosaic-activating mutations in the PIK3CA gene. While various genetic defects have been identified as possible causative factors for KTS, including overexpression of the angiogenic factor VG5Q and a de novo supernumerary ring chromosome 18, several studies indicate that most patients with KTS carry postzygotic somatic mutations in the phosphatidylinositol-4, 5-bisphospate 3-kinase, catalytic subunit alpha (PIK3CA) gene.

Parkes-Weber Syndrome—As used herein, "Parkes-Weber syndrome" refers to a condition characterized by a large capillary malformation on an extremity, soft tissue and bone hypertrophy of the affected limb, and multiple, microscopic, fast-flow arteriovenous shunts. The capillary malformation of Parkes-Weber syndrome is indistinguishable from the port wine stain seen in KTS. Ultrasonography, MRI, and magnetic resonance arteriography are helpful in differentiating Parkes-Weber syndrome from KTS.

CLOVES Syndrome—As used herein, "CLOVES syndrome" refers to congenital lipomatous overgrowth, vascular malformations, epidermal nevi and skeletal anomalies/scoliosis is a very rare congenital overgrowth syndrome resulting from post-zygotic activating mutations in the PIK3CA gene.

Macrocephaly-Capillary Malformation Syndrome—As used herein, "macrocephaly-capillary malformation (M-CM) syndrome" (previously named macrocephaly-cutis marmorata telangiectatica congenita) refers to a genetic syndrome characterized by an enlarged head circumference and patchy, reticular capillary malformations. It is caused by mutations in the PIK3CA gene, leading to gain of function and activation of the PI3K-AKT pathway, which is involved in cell growth, proliferation, survival, and apoptosis. The capillary malformations are usually reticulated and widespread on the trunk and extremities. Cardiac abnormalities including aortic coarctation have also been described. Neuroimaging findings include white matter abnormalities, ventriculomegaly, cerebral asymmetry, cortical dysplasia, polymicrogyria-like changes, and cerebellar tonsil herniation.

Acne Rosacea—Additionally, acne rosacea is a vascular proliferative condition that the inventor expects will respond to treatment with a topical mTOR inhibitor. Acne rosacea, also known simply as "rosacea," is a common chronic vascular inflammatory condition characterized by erythema, telangiectasia, papules and pustules, and occasionally soft tissue hypertrophy (including rhinophyma), typically located on the face. The pathophysiology of rosacea is thought to be multifactorial; however, this common condition is known to present with clinical erythema and vascular manifestations such as telangiectasias. In fact, angiogenesis itself has been reported to play an important role in the pathogenesis of rosacea. Currently available treatments are numerous but often suboptimal. Basic science and other research studies have demonstrated the effectiveness of mTOR inhibitors in decreasing angiogenesis in other models. Hence, as rosacea is known to be associated with vascular proliferation and angiogenesis, the inventor expects that topical mTOR inhibitors such as topical rapamycin will be effective in the treatment of acne rosacea.

Periorificial Dermatitis—Periorificial dermatitis, also known as perioral dermatitis, is another common acneiform condition that presents in children and young adults. Periorificial dermatitis is often considered a juvenile form of acne rosacea as they share overlapping histologic features. Hence, the inventor also believes topical mTOR inhibitors such as topical rapamycin will be effective in the treatment of periorificial dermatitis.

Fibrous Papules—Fibrous papules of the nose (also called fibrous papules of the face or facial angiofibromas) are skin-colored to white, firm, 1 to 3 mm papules that usually occur singly or in small numbers, often on the nose or midface, in late adulthood. Histologically, these lesions resemble angiofibromas and show a normal epidermis, sometimes with an increased number of clear cells overlying the lesion, increased dermal collagen with ectatic blood vessels, and increased dermal cellularity composed of mono- and multinucleated cells with a histiocyte-like appearance. Hence, due to their histological similarity to angiofibromas, the inventor believes topical mTOR inhibitors such as topical rapamycin will be effective in the treatment of fibrous papules.

Acne Vulgaris—As used herein, "acne vulgaris" refers to a disease of the pilosebaceous follicles, characterized by comedones, papules, pustules, sometimes cysts or nodules or even scars. Although comedones are the primary lesion in acne vulgaris, it often presents with inflammatory papules on the skin. Many factors contribute to the develop of acne including blocked pores, microorganisms that lead to release of mediators that cause an inflammatory response resulting in inflamed papules. On pathology, nodular lesions can have proliferation of fibroblasts. Current treatment options are numerous, including topical and oral retinoids, other topical comedolytics, and antibiotics. Since the papular, pustular, and nodular forms of acne have an inflamed, erythematous, and at times proliferative appearance, the inventor believes topical mTOR inhibitors such as topical rapamycin will be effective in the treatment of acne vulgaris.

Capillary Malformation-Arteriovenous Malformation (CM-AVM) Syndrome—As used herein, "capillary malformation-arteriovenous malformation (CM-AVM) syndrome refers to a condition characterized by the combination of congenital and acquired capillary malformations and an AVM of the soft tissue or central nervous system. Infants are often born with multiple pink patches, which may mimic a hemangioma precursor, or a larger CM. The pink patches often increase in number with maturity. The disease is caused by mutations of RASA1. CM-AVM is inherited as an autosomal dominant trait, with wide expressivity. Some affected family members may have symptomatic AVMs, whereas others exhibit only small, pink patches, however the true incidence of underlying AVM is not fully understood because not all individuals have undergone complete evaluation. In the families that have been evaluated, approximately two-thirds of individuals will have the AVM located in the soft tissue and one-third in the central nervous system. In many patients, the AVM will underlie the largest CM. Parkes-Weber syndrome (see below) is one of the ways CM-AVM will present and may do so in the neonatal period with an enlarged limb, overlying CM and an underlying fast-flow AVM or AVF, or vein of Galen malformation which can lead to cardiac compromise.

Methods

An aspect of the invention is a method of treating a cutaneous proliferative condition, comprising topically administering to an affected area of a subject in need thereof a therapeutically effective amount of a mammalian target of rapamycin (mTOR) inhibitor, thereby treating the condition.

As used herein, a "cutaneous proliferative condition" refers to refers to a skin condition characterized by abnormal or undesirable proliferation of principally non-vascular structures or non-vascular tissue in skin. As used herein, "skin" refers to any or all of epidermis, dermis, and hypodermis, and appendages, glands, and blood and lymphatic vessels therein. See, for example, Bloom and Fawcett, A Textbook of Histology, 10$^{th}$ Ed., W. B. Saunders, Philadelphia, 1975.

To the extent that any cutaneous vascular condition as defined herein is considered to be, or can be considered to be, a cutaneous proliferative condition, such cutaneous vascular condition is to be understood also to be included among cutaneous proliferative conditions in accordance with the invention.

In certain embodiments, the cutaneous proliferative condition excludes any one or more of trichoepithelioma and familial multiple discoid fibroma.

Cutaneous proliferative conditions include, without limitation, histiocytosis, scars, hypertrophic or keloidal scars, Proteus syndrome, PTEN hamartoma tumor syndromes, Cowden syndrome, Babbayan-Riley-Ruvalcaba syndrome, cutaneous malignancies and tumors associated with PI3K/AKT/mTOR mutations, keratoderma, acanthosis nigricans, Birt-Hogg-Dubé syndrome, Brooke-Spiegler syndrome, cylindromas, and epidermal nevi.

In certain embodiments, the cutaneous proliferative condition is histiocytosis.

In certain embodiments, the cutaneous proliferative condition is scars.

In certain embodiments, the cutaneous proliferative condition is hypertrophic scars.

In certain embodiments, the cutaneous proliferative condition is keloids.

In certain embodiments, the cutaneous proliferative condition is Proteus syndrome.

In certain embodiments, the cutaneous proliferative condition is PTEN hamartoma tumor syndromes.

In certain embodiments, the cutaneous proliferative condition is Cowden syndrome.

In certain embodiments, the cutaneous proliferative condition is Babbayan-Riley-Ruvalcaba syndrome.

In certain embodiments, the cutaneous proliferative condition is cutaneous malignancies and tumors associated with PI3K/AKT/mTOR mutations.

In certain embodiments, the cutaneous proliferative condition is keratoderma.

In certain embodiments, the cutaneous proliferative condition is acanthosis nigricans.

In certain embodiments, the cutaneous proliferative condition is Birt-Hogg-Dubé syndrome.

In certain embodiments, the cutaneous proliferative condition is Brooke-Spiegler syndrome.

In certain embodiments, the cutaneous proliferative condition is cylindroma.

In certain embodiments, the cutaneous proliferative condition is epidermal nevi.

In certain embodiments, the cutaneous vascular condition excludes histiocytosis.

In certain embodiments, the cutaneous proliferative condition excludes scars.

In certain embodiments, the cutaneous proliferative condition excludes hypertrophic scars.

In certain embodiments, the cutaneous proliferative condition excludes keloids.

In certain embodiments, the cutaneous proliferative condition excludes Proteus syndrome.

In certain embodiments, the cutaneous proliferative condition excludes PTEN hamartoma tumor syndromes.

In certain embodiments, the cutaneous proliferative condition excludes Cowden syndrome.

In certain embodiments, the cutaneous proliferative condition excludes Babbayan-Riley-Ruvalcaba syndrome.

In certain embodiments, the cutaneous proliferative condition excludes cutaneous malignancies and tumors associated with PI3K/AKT/mTOR mutations.

In certain embodiments, the cutaneous proliferative condition excludes keratoderma.

In certain embodiments, the cutaneous proliferative condition excludes acanthosis nigricans.

In certain embodiments, the cutaneous proliferative condition excludes Birt-Hogg-Dubé syndrome.

In certain embodiments, the cutaneous proliferative condition excludes Brooke-Spiegler syndrome.

In certain embodiments, the cutaneous proliferative condition excludes cylindroma.

In certain embodiments, the cutaneous proliferative condition excludes epidermal nevi.

Histiocytosis includes, without limitation, Langerhans cell histiocytosis and non-Langerhans cell histiocytosis (non-LCH).

Langerhans cell histiocytosis includes, without limitation, histiocytosis X, eosinophilic granuloma, Letterer-Siwe disease, Hand-Schuller-Christian syndrome, and Hashimoto-Pritzker syndrome.

In certain embodiments, the histiocytosis is Langerhans cell histiocytosis.

In certain embodiments, the histiocytosis is histiocytosis X.

In certain embodiments, the histiocytosis is eosinophilic granuloma.

In certain embodiments, the histiocytosis is Letterer-Siwe disease.

In certain embodiments, the histiocytosis is Hand-Schuller-Christian syndrome.

In certain embodiments, the histiocytosis is Hashimoto-Pritzker syndrome.

In certain embodiments, the histiocytosis excludes Langerhans cell histiocytosis.

In certain embodiments, the histiocytosis excludes histiocytosis X.

In certain embodiments, the histiocytosis excludes eosinophilic granuloma.

In certain embodiments, the histiocytosis excludes Letterer-Siwe disease.

In certain embodiments, the histiocytosis excludes Hand-Schuller-Christian syndrome.

In certain embodiments, the histiocytosis excludes Hashimoto-Pritzker syndrome.

Non-Langerhans cell histiocytosis (non-LCH) includes, without limitation, benign cephalic histiocytosis (BCH), juvenile xanthogranuloma, xanthoma disseminatum, necrobiotic xanthogranuloma, generalized eruptive histiocytoma, progressive nodular histiocytoma, indeterminate cell histiocytosis, multicentric reticulohistiocytosis, and sinus histiocytosis with massive lymphadenopathy.

In certain embodiments, the histiocytosis is non-Langerhans cell histiocytosis (non-LCH).

In certain embodiments, the histiocytosis is cephalic histiocytosis (BCH).

In certain embodiments, the histiocytosis is juvenile xanthogranuloma.

In certain embodiments, the histiocytosis is xanthoma disseminatum.

In certain embodiments, the histiocytosis is necrobiotic xanthogranuloma.

In certain embodiments, the histiocytosis is generalized eruptive histiocytoma.

In certain embodiments, the histiocytosis is progressive nodular histiocytoma.

In certain embodiments, the histiocytosis is indeterminate cell histiocytosis.

In certain embodiments, the histiocytosis is multicentric reticulohistiocytosis.

In certain embodiments, the histiocytosis is sinus histiocytosis with massive lymphadenopathy.

In certain embodiments, the histiocytosis excludes non-Langerhans cell histiocytosis (non-LCH).

In certain embodiments, the histiocytosis excludes cephalic histiocytosis (BCH).

In certain embodiments, the histiocytosis excludes juvenile xanthogranuloma.

In certain embodiments, the histiocytosis excludes xanthoma disseminatum.

In certain embodiments, the histiocytosis excludes necrobiotic xanthogranuloma.

In certain embodiments, the histiocytosis excludes generalized eruptive histiocytoma.

In certain embodiments, the histiocytosis excludes progressive nodular histiocytoma.

In certain embodiments, the histiocytosis excludes indeterminate cell histiocytosis.

In certain embodiments, the histiocytosis excludes multicentric reticulohistiocytosis.

In certain embodiments, the histiocytosis excludes sinus histiocytosis with massive lymphadenopathy.

As used herein, "topically administering" refers to applying to a surface of skin. Such administering can be achieved by any suitable method and means, and it may include rubbing or spreading a pharmaceutically active agent or pharmaceutical composition on the surface of the skin to promote uniformity of distribution and/or enhance absorption into the skin.

As used herein, an "affected area" refers to an area of skin which is clinically involved in the condition to be treated. An affected area can be defined by clinical inspection, with or without benefit of histologic diagnosis (e.g., biopsy).

In certain embodiments, the affected area comprises at least a portion of any one or more of the head, face, and neck.

As used herein, a "subject" refers to a living mammal. In certain embodiments, a subject is a human.

In certain embodiments, the subject is a human less than 18 years of age. In certain embodiments, the subject is a human 1 to less than 6 years of age. In certain embodiments, the subject is a human 6 to less than 10 years of age. In certain embodiments, the subject is a human 10 to less than 14 years of age. In certain embodiments, the subject is a human 14 to less than 18 years of age.

In certain other embodiments, the subject is a human at least 18 years of age.

As used herein, an "effective amount" is an amount that is sufficient to achieve a desired biological effect. As used herein, a "therapeutically effective amount" is an amount that is sufficient to achieve a desired therapeutic effect.

As used herein, "treat" and "treating" refer to reducing and/or ameliorating at least one sign or symptom of a condition of a subject. The reducing can be partial or complete.

In certain embodiments, the mTOR inhibitor is selected from the group consisting of sirolimus and everolimus.

In certain embodiments, the mTOR inhibitor comprises sirolimus.

In certain embodiments, the mTOR inhibitor comprises everolimus.

In certain embodiments, the mTOR inhibitor consists of sirolimus.

In certain embodiments, the mTOR inhibitor consists of everolimus.

In certain embodiments, the mTOR inhibitor is provided as a topical formulation comprising 0.01% to 10% (w/w) of the mTOR inhibitor in a pharmaceutically acceptable carrier.

In certain embodiments, the mTOR inhibitor is provided as a topical formulation comprising 0.05% to 5% (w/w) of the mTOR inhibitor in a pharmaceutically acceptable carrier.

In certain embodiments, the mTOR inhibitor is provided as a topical formulation comprising 0.1% to 2% (w/w) of the mTOR inhibitor in a pharmaceutically acceptable carrier.

In certain embodiments, the mTOR inhibitor is provided as a topical formulation consisting of 0.01% to 10% (w/v) of the mTOR inhibitor in a pharmaceutically acceptable carrier.

In certain embodiments, the mTOR inhibitor is provided as a topical formulation consisting of 0.05% to 5% (w/v) of the mTOR inhibitor in a pharmaceutically acceptable carrier.

In certain embodiments, the mTOR inhibitor is provided as a topical formulation consisting of 0.1% to 2% (w/v) of the mTOR inhibitor in a pharmaceutically acceptable carrier.

In accordance with each of the foregoing embodiments, in certain embodiments the mTOR inhibitor is provided in combination with a PI3K inhibitor. For example, dual mTOR/PI3K inhibitors include without limitation dactolisib, BGT226, SF1126, and PKI-587.

An aspect of the invention is a method of treating a cutaneous vascular condition, comprising topically administering to an affected area of a subject in need thereof a therapeutically effective amount of a mammalian target of rapamycin (mTOR) inhibitor, thereby treating the condition.

As used herein, a "cutaneous vascular condition" refers to a skin condition characterized by abnormal or undesirable proliferation of principally vascular structures or vascular tissue in skin.

To the extent that any cutaneous proliferative condition as defined herein is considered to be, or can be considered to be, a cutaneous vascular condition, such cutaneous proliferative condition is to be understood also to be included among cutaneous vascular conditions in accordance with the invention.

In certain embodiments, cutaneous vascular conditions exclude any one or more of facial angiofibromas in tuberous sclerosis, microcystic lymphatic malformations, and port wine stains.

Cutaneous vascular conditions include, without limitation, PIK3CA-related overgrowth spectrum (PROS), venolymphatic malformations, acne, acne rosacea, periorifacial dermatitis (also known as perioral dermatitis), fibrous papules, acne vulgaris, and cutaneous capillary malformation-arteriovenous malformation (CM-AVM) syndrome and other RASopathies.

In certain embodiments, the cutaneous vascular condition is PIK3CA-related overgrowth spectrum (PROS).

In certain embodiments, the cutaneous vascular condition is venolymphatic malformations.

In certain embodiments, the cutaneous vascular condition is acne.

In certain embodiments, the cutaneous vascular condition is acne rosacea.

In certain embodiments, the cutaneous vascular condition is periorifacial dermatitis.

In certain embodiments, the cutaneous vascular condition is fibrous papules.

In certain embodiments, the cutaneous vascular condition is acne vulgaris.

In certain embodiments, the cutaneous vascular condition is cutaneous capillary malformation-arteriovenous malformation (CM-AVM) syndrome.

In certain embodiments, the cutaneous vascular condition is a RASopathy. In certain embodiments, the RASopathy is a neurofibroma.

In certain embodiments, the cutaneous vascular condition excludes PIK3CA-related overgrowth spectrum (PROS).

In certain embodiments, the cutaneous vascular condition excludes a venolymphatic malformation.

In certain embodiments, the cutaneous vascular condition excludes acne.

In certain embodiments, the cutaneous vascular condition excludes acne rosacea.

In certain embodiments, the cutaneous vascular condition excludes periorifacial dermatitis.

In certain embodiments, the cutaneous vascular condition excludes fibrous papules.

In certain embodiments, the cutaneous vascular condition excludes acne vulgaris.

In certain embodiments, the cutaneous vascular condition excludes cutaneous capillary malformation-arteriovenous malformation (CM-AVM) syndrome.

In certain embodiments, the cutaneous vascular condition excludes RASopathy.

In certain embodiments, the cutaneous vascular condition excludes any one or more of facial angiofibromas in tuberous sclerosis, microcystic lymphatic malformations, and port wine stains.

In certain embodiments, the cutaneous vascular condition excludes facial angiofibromas in tuberous sclerosis.

In certain embodiments, the cutaneous vascular condition excludes microcystic lymphatic malformations.

In certain embodiments, the cutaneous vascular condition excludes port wine stains.

In certain embodiments, the affected area comprises at least a portion any one or more of the head, face, and neck.

In certain embodiments, the mTOR inhibitor is selected from the group consisting of sirolimus and everolimus.

In certain embodiments, the mTOR inhibitor comprises sirolimus.

In certain embodiments, the mTOR inhibitor comprises everolimus.

In certain embodiments, the mTOR inhibitor consists of sirolimus.

In certain embodiments, the mTOR inhibitor consists of everolimus.

In certain embodiments, the mTOR inhibitor is provided as a topical formulation comprising 0.01% to 10% (w/w) of the mTOR inhibitor in a pharmaceutically acceptable carrier.

In certain embodiments, the mTOR inhibitor is provided as a topical formulation comprising 0.05% to 5% (w/w) of the mTOR inhibitor in a pharmaceutically acceptable carrier.

In certain embodiments, the mTOR inhibitor is provided as a topical formulation comprising 0.1% to 2% (w/w) of the mTOR inhibitor in a pharmaceutically acceptable carrier.

In certain embodiments, the mTOR inhibitor is provided as a topical formulation consisting of 0.01% to 10% (w/w) of the mTOR inhibitor in a pharmaceutically acceptable carrier.

In certain embodiments, the mTOR inhibitor is provided as a topical formulation consisting of 0.05% to 5% (w/w) of the mTOR inhibitor in a pharmaceutically acceptable carrier.

In certain embodiments, the mTOR inhibitor is provided as a topical formulation consisting of 0.1% to 2% (w/w) of the mTOR inhibitor in a pharmaceutically acceptable carrier.

In accordance with each of the foregoing embodiments, in certain embodiments the mTOR inhibitor is provided in combination with a PI3K inhibitor.

In certain embodiments, the subject is a human less than 18 years of age. In certain embodiments, the subject is a human 1 to less than 6 years of age. In certain embodiments, the subject is a human 6 to less than 10 years of age. In certain embodiments, the subject is a human 10 to less than 14 years of age. In certain embodiments, the subject is a human 14 to less than 18 years of age.

In certain other embodiments, the subject is a human at least 18 years of age.

Formulations

Various commercially available mTOR inhibitors are formulated in oral solution or tablet form. Various commercially available mTOR inhibitors are also formulated for intravenous administration. In accordance with certain embodiments of the present invention, mTOR inhibitor is formulated primarily for topical administration. Currently there is no standard or commercially available topical formulation for sirolimus. Currently there is also no standard or commercially available topical formulation for everolimus.

mTOR inhibitor can be formulated for topical administration as a solution, cream, ointment, dispersion, gel, or the like. Such formulations can be prepared in accordance with standard pharmaceutical formulation practices. See, for example, Remington's Pharmaceutical Sciences, 17$^{th}$ Ed., 1985. For example, tablet form mTOR inhibitor can be ground into a powder and combined with a suitable pharmaceutically acceptable carrier.

Topical formulations generally include active pharmaceutical ingredient (mTOR inhibitor) in a concentration of about 0.01 to about 10.0 percent (w/w) or about 0.01 to about 10.0 percent (w/v). In certain embodiments, the formulation includes mTOR inhibitor in a concentration of about 0.05 to about 5.0 percent (w/w) or about 0.05 to about 5.0 percent (w/v). In certain embodiments, the formulation includes mTOR inhibitor in a concentration of about 0.1 to about 10.0 percent (w/w) or about 0.1 to about 10.0 percent (w/v). In certain embodiments, the formulation includes mTOR inhibitor in a concentration of about 0.5 to about 5.0 percent (w/w) or about 0.5 to about 5.0 percent (w/v). In certain embodiments, the formulation includes mTOR inhibitor in a concentration of about 0.1 to about 2.0 percent (w/w) or about 0.1 to about 2.0 percent (w/v).

In certain embodiments, the formulation includes mTOR inhibitor in a concentration of about 1.0 percent (w/w) or about 1.0 percent (w/v). In certain embodiments, the formulation includes mTOR inhibitor in a concentration of 1.0 percent (w/w) or 1.0 percent (w/v).

In certain embodiments, the formulation includes mTOR inhibitor in a concentration of about 2.0 percent (w/w) or about 2.0 percent (w/v). In certain embodiments, the formulation includes mTOR inhibitor in a concentration of 2.0 percent (w/w) or 2.0 percent (w/v).

Formulations in accordance with the invention can further include at least one additional pharmaceutically active agent. For example, in certain embodiments a formulation in accordance with the invention can further include a PI3K inhibitor such as alpelisib, buparlisib, copanlisib, dactolisib, duvelisib, idelalisib, perifosine, pictilisib, taselisib, umbralisib, voxtalisib, AEZS-136, CAL263, CUDC-907, GNE-477, GSK 1059615, IC87114, INK1117, IPI-549, ME-401, palomid 529, PI-103, PWT33597, PX-866, RP6503, RP6530, SF1126, TG100-115, XL 147 (also known as SAR245408), and ZSTK474. Dual mTOR/P13K (inhibitors include without limitation dactolisib, BGT226, SF1126, and PK1-587.

Formulations in accordance with the invention can further include at least one additional agent selected from the group consisting of stabilizers, preservatives, colorants, fragrances, pH buffering agents, lubricants, penetration enhancers, texture enhancers, and the like.

Pharmaceutical Compositions

The formulations described just above can be provided as pharmaceutical compositions. Such pharmaceutical compositions can be made by combining a pharmaceutically active amount of mTOR inhibitor and a pharmaceutically acceptable carrier suitable for topical administration.

Dosing mTOR inhibitor formulated for topical administration is administered up to four times a day to affected area or areas of skin. In certain embodiments, mTOR inhibitor formulated for topical administration is administered once a day. In certain embodiments, mTOR inhibitor formulated for topical administration is administered twice a day. In certain embodiments, mTOR inhibitor formulated for topical administration is administered three times a day. In certain embodiments, mTOR inhibitor formulated for topical administration is administered four times a day.

In certain embodiments, mTOR inhibitor formulated for topical administration is administered once every other day. In certain embodiments, mTOR inhibitor formulated for topical administration is administered once every three days. In certain embodiments, mTOR inhibitor formulated for topical administration is administered once every four days. In certain embodiments, mTOR inhibitor formulated for topical administration is administered once every five days. In certain embodiments, mTOR inhibitor formulated for topical administration is administered once every six days. In certain embodiments, mTOR inhibitor formulated for topical administration is administered once week.

Dosing frequency can be adjusted up or down based on clinical response to treatment.

Dosing can be based on preclinical and/or clinical experience as well as factors such as the nature and severity of the condition to be treated, skin integrity, other patient characteristics such as age and other medical conditions, and judgment of the prescribing physician or other health care provider.

EXAMPLES

Example 1. Treatment of Non-Langerhans Cell Histiocytosis (Non-LCH) with Topical Sirolimus This example describes a patient with biopsy-proven extensive non-LCH diagnosed with extensive BCH which clinically responded to twice daily application of 1% topical rapamycin ointment (compounded at a local pharmacy from tablets). A 5-year-old Caucasian male presented to our clinic for a 3.5 year history of tan-pink macules and papules that began on his face at approximately 15 months of age. A biopsy done from the left cheek at an outside facility was consistent with non-Langerhans cell histiocytosis (non-LCH). By 2.5 years of age, the lesions had progressed to involve the trunk and upper extremities. Additional biopsies showed a diffuse dermal histiocytic and epithelioid cell infiltrate admixed with occasional neutrophils and eosinophils. The infiltrate stained positive for CD68 and factor XIIIa while CD1a and S100 were negative, a pattern consistent with non-LCH. Based on immunohistopathology showing non-LCH, the early age of onset with initiation on the head and neck, as well as the progressive, extensive nature of the lesions, the diagnosis was most consistent with benign cephalic histiocytosis (BCH). The diagnosis was less consistent with other non-LCH such as juvenile xanthogranulomas (which are typically more focal) and generalized eruptive histiocytoma (which generally occur in crops that remit spontaneously). Treatment was desired by the family given the extent of involvement and school age of the child.

Topical rapamycin (1%) compounded in ointment was initiated to the left face with the right face serving as a control. Sirolimus blood levels were negative at 1 month. Subsequent follow up at 6 and 9 months showed fewer new lesions and as well as flattening and fading color of the lesions on the left face compared to the right. After unilateral treatment of one side of the face showed significant improvement in size and number of lesions in comparison to the untreated side, we then treated both sides of the face and noted continued improvement on both sides.

Currently, there is no established treatment for non-LCH such as BCH; hence, treatment with topical mTOR inhibitor such as rapamycin is useful. Based on success of this treatment, inventor expects that all cutaneous involvement and cutaneous presentations of histiocytosis (Langerhans cell histiocytosis including histiocytosis X, eosinophilic granuloma, Letterer-Siwe disease, Hand-Schuller-Christian syndrome, and Hashimoto-Pritzker syndrome; non-LCH including juvenile xanthogranuloma, xanthoma disseminatum, benign cephalic histiocytosis, necrobiotic xanthogranuloma, generalized eruptive histiocytoma, progressive nodular histiocytoma, indeterminate cell histiocytosis, multicentric reticulohistiocytosis, sinus histiocytosis with massive lymphadenopathy) would also respond to treatment with topical rapamycin in similar fashion. As this experience demonstrated clinical effectiveness of topical rapamycin, inventor expects that topical topical administration of any mTOR inhibitor would be effective in the treatment of cutaneous histiocytosis. Additionally, based on this result, inventor expects any topical mTOR inhibitor to be effective in the treatment of any cutaneous proliferative condition.

Example 2. Treatment of Venolymphatic Malformation with Topical Sirolimus

A 14-year-old female presented with a birthmark on the left thigh, present since birth. MRI/MRV revealed a low flow venolymphatic malformation confined to the subcutaneous fat with no visual draining veins. Clinically, it appeared most consistent with a mixed venolymphatic malformation, possibly with a small capillary component to it. Over the last few years, it began scabbing and occasionally bleeding at the surface. The deeper areas sometimes caused a throbbing pain. A decision was made to start treatment with topical 1% sirolimus cream twice a day. After 1.5 to 2 months treatment, the birthmark started to improve. Before starting topical sirolimus, she had painful episodes (6/10 severity) 2-3×per week that lasted 15-20 minutes. After only 1-2 months of using topical sirolimus, she now had one episode of pain every 3 weeks and now the pain only lasted about 10 minutes. Also, the color improved, lightening some, and the crusting was much improved. Additionally, overall the lesion was much flatter since starting the topical sirolimus. Her quality of life improved now that she was is in much less pain.

Previous reports have shown effectiveness of oral sirolimus in the treatment of venolymphatic malformations; however, to the best of inventor's knowledge, topical treatment has never been reported. This patient's venolymphatic malformation improved both symptomatically and improved in appearance with topical 1% rapamycin treatment. Hence, inventor expects that all topical mTOR inhibitors would produce a similar clinical improvement in the treatment of venolymphatic malformations. Additionally, inventor expects that all superficial or cutaneous vascular malformations and cutaneous vascular conditions would respond to treatment with topical mTOR inhibitor.

Example 3. Treatment of Capillary Malformation-Arteriovenous Malformation (CM-AVM) Syndrome with Topical Sirolimus A 17-year-old female presented with several well demarcated pink to slightly tan patches with perilesional halos/rims of pallor scattered on her body, including one on her face. Many of those birthmarks were present since birth or at least since a very young age. The patient's mother also had similar-appearing birthmarks. The patient was otherwise well. Genetic testing confirmed a pathogenic variant identified in RASA1 gene consistent with capillary malformation-arteriovenous malformation (CM-AVM) syndrome. Per the patient and her mother's interest in a topical treatment, off-label use of topical 1% rapamycin cream was used twice a day to the lesion on the face. After several months of use, the patient and her mother both reported that the birthmark had improved in appearance and lessened in visibility. The treatment was tolerated well without side effects. Hence, inventor expects that all topical mTOR inhibitors would produce a similar clinical improvement in the treatment of CM-AVM and in cutaneous involvement of all RASopathies.

Example 4. Treatment of Keloids with Topical Sirolimus

A 51-year-old Caucasian female with a history of burns affecting~40% body surface area status post grafting, complicated by keloids, hypertrophic scars, and contractures, status post treatment with both pulsed dye laser and fractional $CO_2$ laser, had persistent pain, itch, contractures, and tightness in the scars. As an adjuvant treatment, she treated her worst keloidal, contracted scar on her thigh with 1% topical rapamycin one to two times a day. After 1 month of treatment, there was softening and flattening of the areas treated with topical rapamycin. She tolerated the treatment well without any known side effects. Hence, inventor expects that all topical mTOR inhibitors would produce a similar clinical improvement in the treatment all scars and keloids and all cutaneous proliferative or vascular conditions.

We claim:

1. A method of treating a cutaneous proliferative condition, comprising topically administering to an affected area of a subject in need thereof a therapeutically effective amount of a mammalian target of rapamycin (mTOR) inhibitor, thereby treating the condition, wherein the cutaneous proliferative condition is a cutaneous histiocytosis, wherein the mTOR inhibitor is selected from the group consisting of sirolimus and everolimus and is provided as a topical formulation comprising 0.01% to 10% (w/w) of the mTOR inhibitor in a pharmaceutically acceptable carrier.

2. The method of claim 1, wherein the cutaneous proliferative condition is selected from the group consisting of Langerhans cell histiocytosis, non-Langerhans cell histiocytosis (non-LCH).

3. The method of claim 1, wherein the affected area comprises at least a portion any one or more of the head, face, and neck.

4. The method of claim 1, wherein the mTOR inhibitor is sirolimus.

5. The method of claim 1, wherein the mTOR inhibitor is everolimus.

6. The method of claim 1, wherein the subject is a human of less than 18 years of age.

7. The method of claim 1, wherein the subject is a human at least 18 years of age.

8. The method of claim 2, wherein the histiocytosis is selected from the group consisting of eosinophilic granuloma, Letterer-Siwe disease, Hand-Schuller-Christian syndrome, Hashimoto-Pritzker syndrome, benign cephalic histiocytosis (BCH), juvenile xanthogranuloma, xanthoma disseminatum, necrobiotic xanthogranuloma, generalized eruptive histiocytoma, progressive nodular histiocytoma, indeterminate cell histiocytosis, multicentric reticulohistiocytosis, and sinus histiocytosis with massive lymphadenopathy.

9. The method of claim 1, wherein the topical formulation comprises 1% of the mTOR inhibitor in a pharmaceutically acceptable carrier.

* * * * *